US010934343B2

(12) United States Patent
Debret et al.

(10) Patent No.: US 10,934,343 B2
(45) Date of Patent: Mar. 2, 2021

(54) POLYPEPTIDE DERIVED FROM TROPOELASTIN AND BIOCOMPATIBLE MATERIAL COMPRISING SAME

(71) Applicants: CENTRE NATIONAL DE LA RECHERCHE SCIENTIFIQUE, Paris (FR); UNIVERSITÉ CLAUDE BERNARD LYON 1, Villeurbanne (FR)

(72) Inventors: Romain Debret, Lyons (FR); Clément Faye, Campagne (FR); Jérôme Sohier, Lyons (FR); Pascal Sommer, Marseilles (FR)

(73) Assignees: CENTRE NATIONAL DE LA RECHERCHE SCIENTIFIQUE, Paris (FR); UNIVERSITÉ CLAUDE BERNARD LYON 1, Villeurbanne (FR)

( * ) Notice: Subject to any disclaimer, the term of this patent is extended or adjusted under 35 U.S.C. 154(b) by 0 days.

(21) Appl. No.: 16/301,422

(22) PCT Filed: May 12, 2017

(86) PCT No.: PCT/EP2017/061517
§ 371 (c)(1),
(2) Date: Nov. 13, 2018

(87) PCT Pub. No.: WO2017/194761
PCT Pub. Date: Nov. 16, 2017

(65) Prior Publication Data
US 2019/0169269 A1 Jun. 6, 2019

(30) Foreign Application Priority Data

May 13, 2016 (FR) ..................... 16 54306

(51) Int. Cl.
A61K 38/17 (2006.01)
C07K 14/78 (2006.01)
C12M 3/00 (2006.01)
A61K 38/39 (2006.01)
A61L 27/22 (2006.01)
A61L 27/52 (2006.01)
A61L 27/56 (2006.01)
C12N 5/071 (2010.01)

(52) U.S. Cl.
CPC .............. *C07K 14/78* (2013.01); *A61K 38/39* (2013.01); *A61L 27/227* (2013.01); *A61L 27/52* (2013.01); *A61L 27/56* (2013.01); *C12M 3/00* (2013.01); *C12N 5/0625* (2013.01); *A61L 2430/34* (2013.01); *C12N 2533/50* (2013.01)

(58) Field of Classification Search
None
See application file for complete search history.

(56) References Cited

FOREIGN PATENT DOCUMENTS

WO    99/03886 A1    1/1999
WO    2010/119420 A1    10/2010

OTHER PUBLICATIONS

UniProt Database, Accession No. P04985, 12 pages (1987) (Year: 1987).*
Merriam Webster, "Successive", available online at https://www.merriam-webster.com/dictionary/successive, 11 pages (accessed on Apr. 26, 2020) (Year: 2020).*
Bandiera Antonella et al.: "Expression and characterization of human-elastin-repeat-based temperature-responsive protein polymers for biotechnological purposes", Biotechnology and Applied Biochemistry, Academic Press, US, vol. 42, No. 3, Dec. 1, 2005, pp. 247-256.
Gianni Ciofani et al. : "Human recombinant elastin-like protein coatings for muscle cell proliferation and differentiation", Acta Biomaterialia, Amsterdam, NL, vol. 9, No. 2, Feb. 1, 2013, pp. 5111-5121.
Bandiera Antonella et al.: "Phase transition and particle formation of a Human Elastin-Like polypeptide", Bioengineering Conference, 2009 IEEE 35th Annual Northeast, IEEE, Piscataway, NJ, USA, Apr. 3, 2009, pp. 1-2.
Database Geneseq: "Human elastin-like polypeptide (HELP) 12 sequence, SEQ ID No. 1# 3.", Dec. 9, 2010.
Giselle C. Yeo et al.: "Fabricated Elastin", Advanced Healthcare Materials, vol. 4, No. 16, DE, Nov. 1, 2015, pp. 2530-2556.
Steven G. Wise et al.: "Tropoelastin: A versatile, bioactive assembly module", Acta Biomaterialia, Amsterdam, NL, vol. 10, No. 4, Apr. 1, 2014, pp. 1532-1541.
D.V. Bax et al.: "Cell Adhesion to Tropoelastin Is Mediated via the C-terminal GRKRK Motif and Integrin alpha-V-beta-3", Journal of Biological Chemistry, US, vol. 284, No. 42, Oct. 16, 2009, pp. 28616-28623.
International Search Report issued by the International Searching Authority in International Application No. PCT/EP2017/061517, dated Apr. 6, 2018, 4 pages.

* cited by examiner

*Primary Examiner* — Thea D'Ambrosio
(74) *Attorney, Agent, or Firm* — Troutman Pepper Hamilton Sanders LLP

(57) ABSTRACT

The present invention provides a tropoelastin-derived polypeptide and an elastic composite biocompatible material comprising the polypeptide. The object of the invention is also a method for the synthesis of such a biocompatible material, a cell culture support comprising such a biocompatible material and the use of this material, in particular in the biological and medical field, in particular for cell culture and tissue regeneration.

Figure 1:
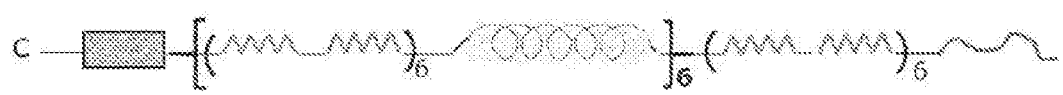

12 Claims, 12 Drawing Sheets
Specification includes a Sequence Listing.

C-DYKDDDDK-{(VGVAPG-VGVLPG)₆-AAAKAAAKAAK}₆-(VGVAPG-VGVLPG)₆-GGACLGKACGRKRK

SEQ ID NO: 9

A

B

FIG 14A, 14B, 14C, 14D
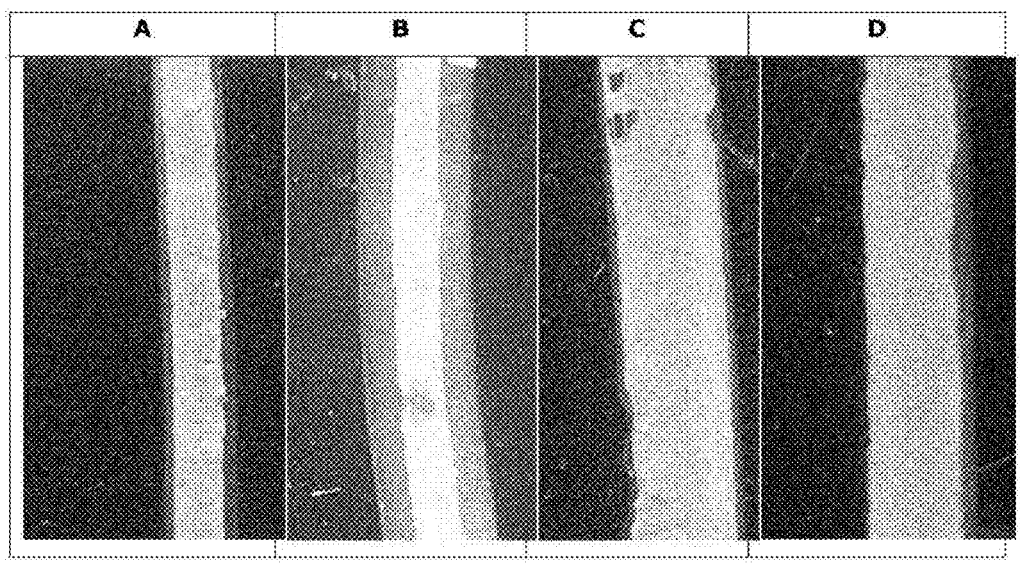
FIG 15A, 15B
FIG 15A
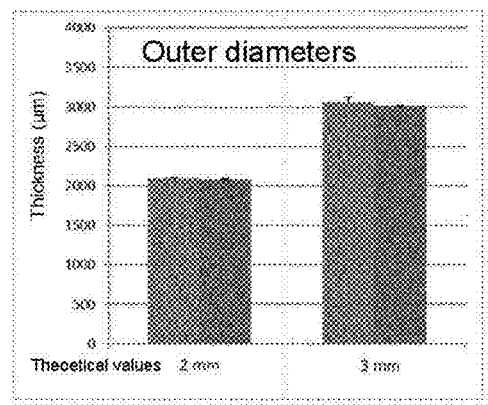
FIG 15B
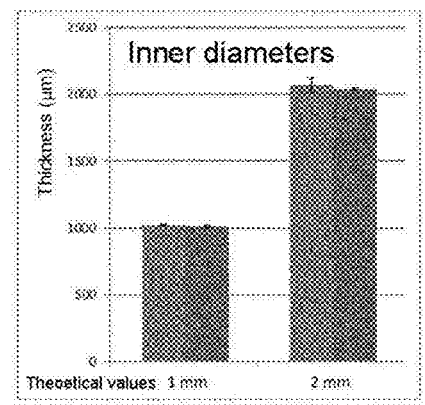

POLYPEPTIDE DERIVED FROM TROPOELASTIN AND BIOCOMPATIBLE MATERIAL COMPRISING SAME

CROSS-REFERENCE TO RELATED APPLICATIONS

This application is a U.S. National Phase of International Patent Application No. PCT/EP2017/061517, filed May 12, 2017, which claims priority to French Patent Application No. 16 54306, filed on May 13, 2016. The entire contents of these applications are hereby incorporated by reference in their entireties.

SEQUENCE LISTING

This application contains a Sequence Listing which has been submitted in ASCII format via EFS-Web and is hereby incorporated by reference herein in its entirety. The ASCII text file created on Nov. 13, 2018, is named 36971800seqlist.txt and is 33,700 bytes in size.

The present invention relates to a polypeptide derived from tropoelastin and a composite biocompatible material comprising the polypeptide. It also relates to a method for synthesizing such a biocompatible material, as well as the application of this material, in particular in the biological and medical field, and, in particular, for cell culture and tissue engineering. The invention is therefore in the field of the biochemistry of polypeptides and composite biomaterials based on proteins.

Known tissue engineering supports, which may be prepared from natural components such as chitosan, collagen, hyaluronic acid or alginate, or synthetic components, such as organic polymers, are all subject to the same limit due to the current impossibility of reproducing a tissue with elastic properties similar to the sought tissues. This limit is the result, in particular, of the absence of matrix supports adapted to create the microenvironment having an adequate ratio between the elastic and viscoelastic components of neosynthesized tissues and their support matrices. The commercial supports known to date do not incorporate an elastic component within them, which has the immediate consequence of a contraction of the implanted tissue, which results in a modification of the cellular phenotype and variability of the induced biological responses.

In tissue engineering applications, protein-based biomaterials offer an attractive alternative to synthetic polymers for their potential use as a three-dimensional structure. The cellular microenvironment influences cell behavior through biophysical, mechanical, and tissue-specific biochemical factors. Biomaterials must therefore meet many criteria and must, in particular, be able to reproduce the properties of native tissues, while being biocompatible, non-immunogenic and biodegradable. They must also closely mimic the function of the extracellular matrix in promoting attachment, migration and cell proliferation. Soft tissue engineering is particularly complex because it also requires functional elasticity properties.

Biomaterials comprising polypeptides derived from elastin that incorporate polypeptides composed of repeat pentapeptide sequences prepared by chemical synthesis or recombinantly-synthesized proteins (Annabi et al., 2013) are known. These materials have mechanical and biochemical properties suitable for tissue engineering applications in general, but their in vivo properties have not been studied in detail or specifically with respect to one or more tissues.

A polypeptide derived from human tropoelastin, associated with an RGD (Arginine-Glycine-Aspartic Acid) group (Wise et al, 2014), is also known. However, in order to obtain sufficient 3D structural stability, these molecules must be mixed and shaped with other more rigid polymers, natural or not, and the resulting biomaterials are therefore confronted with the limits mentioned above, i.e. the biocompatibility, the structure, the mechanical properties, the "biological informativity" of the framework, the production in "green chemistry" and the standardization of the production.

Patent EP 1 007 555 describes a derivative of human tropoelastine whose amino acid sequence is derived from the sequence of native tropoelastin. The amino acid sequence of this derivative is homologous, i.e. at least 65% identical with the native tropoelastin sequence as a whole. The polypeptide is capable of binding glycosaminoglycans (GAGs), while its use in the medical field in a support-related form, including as an implant, is mentioned.

Also known are proteins derived from elastin comprising repeats of VPGXG (SEQ ID NO:21) pentapeptide sequences where X represents any natural or modified amino acid with the exception of proline (Yeo et al, 2015). These proteins and their degradation products are biocompatible, have self-assembly capabilities and mechanical properties similar to the native protein, as well as a coacervation ability. The possibility of inserting bioactive sequences in these proteins in order to confer biological functions is mentioned. In vitro, the gels formed from these proteins have been shown to be an extracellular matrix for fibroblasts and neuroblasts (Jeon et al, 2011).

The inventors have now designed, synthesized and characterized in vitro and in vivo a novel protein derived from tropoelastin, inspired by the structure of human tropoelastin and which has the advantage of not having exogenous motifs. A polypeptide derived from elastin (or PDE) according to the invention comprises hydrophobic domains but also crosslinking domains that are also inspired by human tropoelastin. A polypeptide according to the invention is the only polypeptide to date that is derived from elastin (or PDE) comprising the C-terminal region of human tropoelastin (or domain 36) which contains both the RKRK motif (SEQ ID No: 4) that is known to bind to cells on $\alpha_v\beta_3$ integrin, and a disulfide bridge for facilitating the assembly of elastic fibers. Unlike the PDE of the prior art, which are formed by the pentapeptide repeat, the hydrophobic domains of a PDE according to the invention consist of the repeat of hexapeptides. Such a hexapeptide motif is highly conserved in human tropoelastin and has biological activity via the membrane receptor binding the elastin (Elastin Binding Protein or EBP).

The inventors have demonstrated that a protein derived from elastin according to the invention has self-assembly and biodegradability properties. The crosslinked structures comprising a polypeptide according to the invention and a crosslinking agent, on the one hand, as well as the crosslinked structures comprising a polypeptide according to the invention, a bifunctional crosslinking agent and a hydrophilic polymer, on the other hand, have the characteristics of an elastic material, thus benefiting from the biomimetic contribution of the PDE, and are biocompatible and biodegradable. In addition, the high vascularity and the weak inflammatory reaction induced during the in vivo implantation of crosslinked structures comprising a polypeptide according to the invention and a synthetic polymer, demonstrate the high potential of these biocompatible materials for the engineering of elastic tissues.

A polypeptide and a biocompatible material according to the invention thus make it possible to have biomaterials that are modular and may be processed industrially. The modulation of the amino acid sequence and the molecular weight of the polypeptide, as well as the mechanical parameters of the material makes it possible to reproduce the mechanical properties of targeted human elastic tissues. A material according to the invention may be prepared by only using so-called "green chemistry" products and processes according to an easily standardized method, which does not generate toxic or dangerous compounds, even after degradation, and does not require special equipment. Finally, the modular porosity and the unexpected biodegradability of a biocompatible material according to the invention, are assets that facilitate its cell colonization and its replacement by a neo-tissue, which are two favorable criteria in regenerative medicine.

According to a first aspect, the object of the invention is an isolated polypeptide derived from human tropoelastin. In a preferred embodiment, a polypeptide according to the invention comprises the amino acid sequence SEQ ID No: 8 or consists of the amino acid sequence SEQ ID No: 9. The object of the invention is also the nucleotide sequence coding for a polypeptide according to the invention.

According to a second aspect, the object of the invention is a biocompatible crosslinked structure comprising a polypeptide derived from tropoelastine according to the invention. In a first preferred embodiment, such a crosslinked structure comprises a polypeptide according to the invention and a crosslinking agent. In a second preferred embodiment, such a crosslinked structure comprises a polypeptide according to the invention, a crosslinking agent and a hydrophilic polymer.

According to a third aspect, the object of the invention is a method for synthesizing a crosslinked structure according to the invention. In a preferred embodiment, such a method comprises mixing a polypeptide derived from elastin according to the invention, a crosslinking agent and a hydrophilic polymer, followed by casting the mixture in an appropriate mold and under conditions that lead to the generation of pores within the biomaterial, especially in the presence of a suitable pore-forming material.

According to a fourth aspect, the object of the invention is a cell culture support consisting of a biocompatible material according to the invention, and its use in vitro for the cultivation of different types of cells.

Finally, according to a fifth aspect, the object of the invention is a biocompatible material according to the invention with respect to its use for tissue engineering, and preferably for the regeneration of soft tissues, or its use for the synthesis of a composite biomaterial, preferably a composite biomaterial comprising, or consisting of, a biocompatible material according to the invention and another compound, wherein the compound is constituted by a material of synthetic or natural origin.

DETAILED DESCRIPTION

The present invention firstly relates to an isolated polypeptide derived from tropoelastine, the amino acid sequence of which comprises, or consists of, successively, from the N-terminus to the C-terminus of the polypeptide:

A domain comprising at least 2 and at most 40 repeats of a unit comprising
A hydrophobic region (A) comprising successively at least 6 and at most 80 sequences $$X_1GX_2X_3PG \quad \text{(SEQ ID NO: 1)}$$

wherein X $X_1$, $X_2$ and $X_3$ represent a hydrophobic amino acid independently selected from the group consisting of: alanine, valine, leucine and isoleucine; wherein the SEQ ID No: 1 is identical or different,
or a hydrophobic region (A') comprising a sequence having at least 65% identity with the sequence of the hydrophobic region (A), and
A region (B) comprising at least the sequence $$AAAKAAK \quad \text{(SEQ ID NO: 2)}$$

and preferably including the sequence $$AAAKAAAKAAK \quad \text{(SEQ ID NO: 3)}$$

or a region (B') of at least 8 amino acids, comprising at least the AAAKAAK sequence (SEQ ID No: 2) and having at least 65% identity with the sequence SEQ ID No: 3, and
A domain (D) comprising at least two non-consecutive cysteine amino acids and the sequence $$RKRK, \quad \text{(SEQ ID NO: 5)}$$

and preferably including the sequence $$GGACLGKACGRKRK, \quad \text{(SEQ ID NO: 6)}$$

or a sequence comprising obligatorily the sequence SEQ ID No: 5 and having at least 65% identity with the sequence SEQ ID No: 6.

According to a particular aspect, an isolated polypeptide derived from tropoelastin according to the present invention, further comprises a further hydrophobic domain (C), wherein the domain (C) is located between the (B) and (D) domains of the polypeptide. The additional hydrophobic domain (C) comprises successively at least 6 and at most 80 sequences $$X_4GX_5X_6PG \quad \text{(SEQ ID NO: 4)}$$

wherein $X_4$, $X_5$ and $X_6$ are any hydrophobic amino acid except proline; and
wherein the SEQ ID No: 4 is identical or different,
or a hydrophobic domain (C') comprising a sequence having at least 65% identity with the sequence of the hydrophobic domain (C).

According to this particular aspect, the object of the present invention is therefore an isolated polypeptide derived from tropoelastine, the amino acid sequence of which comprises, successively, from the N-terminus to the C-terminus of the polypeptide:

A domain comprising at least 2 and at most 40 repeats of a unit comprising
  A hydrophobic region (A) comprising successively at least 6 and at most 80 sequences $$X_1GX_2X_3PG \quad \text{(SEQ ID NO: 1)}$$

wherein $X_1$, $X_2$ and $X_3$ represent a hydrophobic amino acid independently selected from the group consisting of: alanine, valine, leucine and isoleucine; wherein the SEQ ID No: 1 is identical or different,
  or a hydrophobic region (A') comprising a sequence having at least 65% identity with the sequence of the hydrophobic region (A), and
  A region (B) comprising at least the sequence $$AAAKAAK \quad \text{(SEQ ID NO: 2)}$$

and preferably comprising the sequence $$AAAKAAAKAAK \quad \text{(SEQ ID NO: 3)}$$

or a region (B') of at least 8 amino acids, comprising at least the AAAKAAK sequence (SEQ ID No: 2) and having at least 65% identity with the sequence SEQ ID No: 3,
A hydrophobic domain (C) comprising successively at least 6 and at most 80 sequences $$X_4GX_5X_6PG \quad \text{(SEQ ID NO: 4)}$$

wherein X4, X5 and X6 are any hydrophobic amino acid except proline; wherein the SEQ ID No: 4 is identical or different,
  or a hydrophobic domain (C') comprising a sequence having at least 65% identity with the sequence of the hydrophobic domain (C), and
A domain (D) comprising at least two non-consecutive cysteine amino acids and the sequence $$RKRK, \quad \text{(SEQ ID NO: 5)}$$

and preferably including the sequence $$GGACLGKACGRKRK, \quad \text{(SEQ ID NO: 6)}$$

or a sequence obligatorily comprising the sequence SEQ ID No: 5 and having at least 65% identity with the sequence SEQ ID No: 6.

The term "tropoelastine" refers to a polypeptide having a molecular weight of about 72 kDa, and whose amino acid sequence is publicly available under the reference AAC98394 (version AAC98394.1 GI: 182020, dated 8 Mar. 2002. NCBI database "Protein"). Tropoelastin is encoded by a single ELN gene (GID: 2006, MIM: 130160. NCBI database "Gene"), whose alternative splicing during the expression of the protein leads to the existence of numerous variants (or polymorphs) of tropoelastine. The term "coacervation" refers to the non-covalent aggregation of tropoelastine monomers in the form of spherules, especially via its hydrophobic domains. The covalent binding of multiple tropoelastin molecules leads to the formation of insoluble elastin polymers. The terms "tropoelastin derivative" and "elastin derivative" are used in prior art documents and are considered equivalent when they designate a polypeptide not self-aggregated covalently.

The term "tropoelastin derivative" refers to a polypeptide whose amino acid sequence is organized into successive domains comprising repeat motifs, wherein this organization and these repeat motifs are inspired by native human tropoelastin. Tropoelastin derivatives are distinguished from native tropoelastin in that their amino acid sequence is altered from native tropoelastin by substitution, addition and/or deletion of amino acids.

The term "isolated polypeptide" refers to a polypeptide obtained by a method known to those skilled in the art, and especially recombinantly, or by chemical synthesis, wherein the polypeptide is then separated from its initial environment by partial or total purification. Similarly, the term "isolated nucleic acid" refers to a nucleic acid obtained by a method known to those skilled in the art, and, in particular, according to any known method of genetic engineering or by chemical synthesis, followed by purification of the nucleic acid. An isolated polypeptide according to the invention thus differs from a natural polypeptide, but is not limited to a particular method of preparation or synthesis. Similarly, an isolated nucleic acid according to the invention differs from a natural amino acid while not being limited to a particular method of synthesis.

Preferably, a polypeptide according to the invention is produced recombinantly, according to techniques well known to those skilled in the art. The production of a recombinant protein includes, in particular, the choice of the host intended for production, for example a bacterium, a eukaryotic yeast or mammalian cell or a transgenic animal, and the design of a synthetic nucleotide sequence adapted to the production, including the choice of a production vector and the choice of codons used to optimize production. A recombinant protein may be produced in the form of a fusion protein, which associates the protein of interest with a "tag" domain to enable the identification and/or purification of the protein of interest. The purification of the protein of interest is then carried out according to one of the many protocols accessible to those skilled in the art.

The invention firstly relates to a polypeptide derived from tropoelastine having at least one of the mechanical or biological characteristics of tropoelastin taken in its natural state, especially in that it is capable of exerting a physiological activity, even a partial one, of tropoelastine, such as:
  elasticity property, including, in particular, the return to a folded shape after distension of the molecule, applied under appropriate conditions, and/or
  coacervation ability and/or
  non-covalent self-aggregation ability, and/or covalent aggregation ability with elastin molecules, and/or
  cell adhesion ability in vitro and/or
  cell adhesion ability in vivo and/or
  ability to stimulate cell proliferation and/or
  ability to adhere to $\alpha_v\beta_3$ integrin and/or
  ability to adhere to glycosaminoglycans, and/or
  sensitivity to degradation by a metalloprotein known to degrade elastin, in particular by the metallo-protein matrix-12 (MMP-12).

These properties may be observed or measured by any suitable measuring technique known to those skilled in the art.

According to a particular aspect, the crosslinked structure of a polypeptide according to the invention has elastic properties, which may be measured and quantified by those skilled in the art using one or more known means for determining the mechanical properties of a compound. The tests of the elastic properties include, but are not limited to, an indentation test as described in the present application and any test applied to such a crosslinked structure for determining Young's modulus.

From its N-terminus to its C-terminus, a polypeptide according to the invention comprises two or three domains which will now be described in detail.

When the polypeptide comprises two domains, the first domain comprises, or consists of, the regions designated by (A) and (B), and the other domain corresponds to the region (D), as previously defined.

When, in a more particular aspect of the invention, from its N-terminus to its C-terminus, a polypeptide according to the invention comprises three domains, wherein the first domain comprises, or consists of, the regions designated by (A) and (B), while the second and third domains respectively correspond to the regions (C) and (D) as defined above.

The terms "polypeptide" and "protein" are equivalent and denote a polymer of amino acids. The terms "region" and "domain" refer to a primary sequence of amino acids. Each amino acid is designated by its name or by its abbreviation of three letters or one letter according to IUPAC. The term "amino acid" includes naturally-occurring amino acids, amino acid analogs, (D) and (L) amino acid isomers and amino acid derivatives, such as protected amino acids.

A polypeptide according to the invention comprises a sequence containing the unique characteristics of human tropoelastin, namely hydrophobic domains and more hydrophilic crosslinking domains, whose alternation is responsible for the properties of coacervation and elasticity. A polypeptide according to the invention also comprises, in its C-terminus part, a domain encoded by exon 36, or a domain having at least 65% identity therewith, contributing to the assembly of elastic fibers in man, and comprising the sequence RKRK (SEQ ID NO: 5) which is involved in the binding to the $\alpha_v\beta_3$ integrin.

The term "hydrophobic region" relative to the amino acid sequence of a polypeptide refers to a sequence that is rich in amino acids whose side chain has a hydrophobic or apolar nature. The hydrophobic amino acids have an aliphatic chain composed solely of carbon and hydrogen atoms and may be selected from the group consisting of: alanine, valine, leucine, isoleucine, methionine, phenylalanine, tryptophan, proline, and the like.

The hydrophilic or hydrophobic character of the side chain of an amino acid is defined by its hydropathy index, which makes it possible to determine the hydrophobic nature of a region of a protein by virtue of the amino acid sequence. The more hydrophobic a group is, the stronger is the hydropathy index. The hydropathy profile represents the average value of the hydropathic index of a segment of twenty amino acids centered around a position. A positive value of the index corresponds to hydrophobic behavior of the segment while a negative value corresponds to hydrophilic behavior.

According to particular aspects, in a polypeptide according to the invention, the first domain comprises, or consists of, at least 2 and at most 40, preferably at least 2 and at most 35, at least 2 and at most 30, at least 2 and at most 20, at least 2 and at most 15, at least 2 and at most 10, and more preferably 2, 3, 4, 5, 6, 7, 8, 9 or 10 repeats of a unit comprising:

a hydrophobic region (A), or a hydrophobic region (A') whose amino acid sequence has at least 65% identity with the hydrophobic region (A), and a region (B), or a region (B') whose amino acid sequence has at least 65% identity with the region (B).

According to a particular aspect of a polypeptide according to the invention, the hydrophobic region (A) comprises, or consists of, at least 6 and at most 80 repeat hexapeptide sequences $X_1GX_2X_3PG$ (SEQ ID No: 1), preferably at least 6 and at most 70, at least 6 and at most 60, at least 6 and at most 40, at least 6 and at most 30, at least 6 and at most 20, and more preferably 6, 7, 8, 9, 10, 11, 12, 13, 14, 15, 16, 17, 18 or 19 repeats of hexapeptide sequences $X_1GX_2X_3PG$ (SEQ ID No: 1), wherein SEQ ID No: 1 is identical or different. In the sequence SEQ ID No: 1, $X_1$, $X_2$ and $X_3$ represent a hydrophobic amino acid independently selected from the group consisting of: alanine, valine, leucine and isoleucine.

According to a particular aspect, in a polypeptide according to the invention, the amino acid sequence of the hydrophobic region (A') has at least 65% identity with the sequence of the region (A) and has a globally hydrophobic character.

In the expression "has at least 65% identity with the region", the percentage is purely statistical and the differences between the two nucleotide or amino acid sequences may be randomly distributed over their entire length. The percentage of sequence identity between two sequences is defined after the alignment of the sequences to be compared. When a position in one of the sequences is occupied by the same base or the same amino acid, the molecules are identical at this position. The degree of identity between two sequences is a function of the number of identical positions between the two sequences. Sequence comparisons may be performed using any algorithm for this purpose known to those skilled in the art.

According to a particular aspect of a polypeptide according to the invention, the amino acid sequence of a hydrophobic region (A') has at least 65%, preferably at least 70%, at least 75%, at least 80%, at least 85%, at least 90%, 91%, 92%, 93%, 94%, 95%, 96%, 97%, 98%, at least 99% or 100% identity with the amino acid sequence of the hydrophobic region (A).

In a polypeptide according to the invention, the region (B) is involved in the crosslinking of the polypeptide and comprises, or consists of, at least the AAAKAAK sequence (SEQ ID NO: 2). According to a particular aspect of a polypeptide according to the invention, the crosslinking region (B) comprises, or consists of, at least the sequence AAAKAAAKAAK (SEQ ID NO: 3) or a region (B') of at least 8 amino acids, and whose amino acid sequence has at least 65% identity with the sequence SEQ ID No: 3. Preferably, the region (B') of a polypeptide according to the invention comprises at least one, preferably at least two, and in particular three, lysine amino acids, wherein these lysines are separated by two or three, preferably three, amino acids. The region (B) is capable of forming a secondary structure of the alpha helix type, wherein preferably the region (B') is capable of forming a secondary structure of the alpha helix type.

According to a particular aspect, in a polypeptide according to the invention, the amino acid sequence of the region (B') has at least 65% identity with the sequence (B), preferably at least 70%, at least 75%, at least 80%, at least 85%, at least 90%, 91%, 92%, 93%, 94%, 95%, 96%, 97%, 98%, at least 99% or 100% identity with the amino acid sequence of the region (B).

According to a particular aspect, a polypeptide according to the invention comprises a second domain (C), defined by its hydrophobic character and comprising successively, or consisting of, at least 6 and at most 80 $X_4GX_5X_6PG$ (SEQ ID No: 4) repeat sequences, wherein $X_4$, $X_5$ and $X_6$ represent any amino acid except proline; wherein the SEQ ID No: 4 is identical or different. $X_4$, $X_5$ and $X_6$ are therefore independently selected from the following amino acids: alanine, arginine, asparagine, aspartic acid, glutamine, glutamic acid, glycine, histidine, isoleucine, leucine, lysine, methionine, phenylalanine, tryptophan, serine, threonine, tyrosine and valine, and the like.

According to a more particular aspect, the second hydrophobic domain (C) comprises, or consists of, successively at least 6 and at most 80 $X_4GX_5X_6PG$ (SEQ ID No: 4) repeat sequences, preferably at least 6 and at most 70, at least 6 and at most 60, at least 6 and at most 40, at least 6 and at most 30, at least 6 and at most 20, and more preferably 6, 7, 8, 9, 10, 11, 12, 13, 14, 15, 16, 17, 18 or 19 repeats of hexapeptide sequences $X_4GX_5X_6PG$ (SEQ ID No: 4), wherein $X_4$, $X_5$ and $X_6$ represent a hydrophobic amino acid independently selected from the group consisting of: alanine, valine, leucine, isoleucine; wherein SEQ ID No: 4 is identical or different.

According to a particular aspect, in a polypeptide according to the invention, the amino acid sequence of the region (C') has at least 65% identity with the sequence (C), preferably at least 70%, at least 75%, at least 80%, at least 85%, at least 90%, 91%, 92%, 93%, 94%, 95%, 96%, 97%, 98%, at least 99% or 100% identity with the amino acid sequence of the region (C).

A polypeptide according to the invention comprises a third domain (D) which comprises at least two non-consecutive cysteine amino acids and the sequence RKRK (SEQ ID No: 5). Preferably the domain (D) comprises, or consists of:
the sequence GGACLGKACGRKRK (SEQ ID No: 6), or
a sequence obligatorily comprising the sequence SEQ ID No: 5 and having at least 65% identity with the sequence SEQ ID No: 6.

According to one particular aspect, in a polypeptide according to the invention the two cysteine amino acids of domain (D) are separated by 1, 2, 3, 4, 5, 6, 7 or 8 amino acids, and are preferably separated by 4 amino acids; wherein the cysteines are capable of forming an intrachain disulfide bridge.

The sequence SEQ ID No: 6 is coded by exon 36 of the gene coding for human tropoelastin, wherein this domain is recognized as facilitating the assembly of elastic fibers, and playing a role in cell signaling and the property of binding to GAGs of the protein.

According to a more particular aspect, a polypeptide according to the invention comprises a domain (D) obligatorily comprising the sequence SEQ ID No: 5, and whose amino acid sequence has at least 65% identity, preferably at least 70%, at least 75%, at least 80%, at least 85%, at least 90%, 91%, 92%, 93%, 94%, 95%, 96%, 97%, 98%, at least 99% or 100% identity with the sequence SEQ ID No: 6.

According to an even more particular aspect, the object of the invention is a synthetic polypeptide derived from tropoelastine, whose amino acid sequence comprises, or consists of, successively, from the N-terminus to the C-terminus of the polypeptide:
A domain comprising, or consisting of, at least 2 and at most 40 repeats of a unit comprising:
A hydrophobic region (A) comprising, or consisting of, successively at least 6 and at most 80 $VGVX_7PG$ sequences (SEQ ID NO: 7) wherein $X_7$ is a hydrophobic amino acid selected from the group consisting of: alanine and leucine; wherein the SEQ ID No: 7 is the same or different, or a hydrophobic region (A') comprising a sequence having at least 65% identity with the sequence of the hydrophobic region (A), and
A region (B) comprising at least, or consisting of, the AAAKAAK sequence (SEQ ID No: 2), and preferably comprising the sequence AAAKAAAKAAK (SEQ ID No: 3) or a region (B') of at least 8 amino acids, comprising at least, or consisting of, the AAA-KAAK sequence (SEQ ID No: 2) and having at least 65% identity with the sequence SEQ ID No: 3, and
A hydrophobic domain (C) comprising, or consisting of, successively at least 6 and at most 80 $VGX_7PG$ sequences (SEQ ID No: 7) wherein $X_7$ is a hydrophobic amino acid selected from the group consisting of: alanine and leucine; wherein the SEQ ID No: 7 is the same or different, or a hydrophobic domain (C') comprising, or consisting of, a sequence having at least 65% identity with the sequence of the hydrophobic domain (C), and
A domain (D) comprising at least two non-consecutive cysteine amino acids and the sequence RKRK (SEQ ID No: 5), and preferably comprising, or consisting of, the sequence GGACLGKACGRKRK (SEQ ID No: 6) or a sequence obligatorily comprising the sequence SEQ ID No: 5 and having at least 65% identity with the sequence SEQ ID No: 6.

According to an even more particular aspect, the object of the invention is a synthetic polypeptide derived from tropoelastine, the amino acid sequence of which comprises, or consists of, successively, the N-terminus to the C-terminus of the polypeptide:
A domain comprising, or consisting of, 6 repeats of a unit comprising:
A hydrophobic region (A) comprising, or consisting of, successively at least 3 and at most 40 VGVAPGVGVLPG (SEQ ID No: 10) sequences, preferably at least 3 and at most 35, at least 3 and at most 30, at least 3 and at most 20, at least 4 and at most 15, at least 5 and at most 10, and more preferably 6, 7, 8 or 9 repeats of an amino acid sequence VGVAPGVGVLPG (SEQ ID No: 10),
A region (B) comprising or consisting of the sequence AAAKAAAKAAK (SEQ ID No: 3) or a region (B') of at least eight amino acids comprising at least the AAAKAAK sequence (SEQ ID No: 2) and having at least 65% identity with the sequence SEQ ID No: 3,
A hydrophobic domain (C) comprising, or consisting of, successively at least 3 and at most 40 VGVAPGVGVLPG (SEQ ID No: 10) sequences, preferably at least 3 and at most 35, at least 3 and at most 30, at the at least 3 and at most 20, at least 4 and at most 15, at least 5 and at most 10, and more preferably 6, 7, 8 or 9 repeats of an amino acid sequence VGVAPGVGVLPG (SEQ ID No: 10), and
A domain (D) comprising the sequence GGA-CLGKACGRKRK (SEQ ID No: 6).

According to an even more particular aspect, the object of the invention is a synthetic polypeptide derived from tropoelastine, the amino acid sequence of which comprises, or consists of, successively, the N-terminus to the C-terminus of the polypeptide:
A domain comprising, or consisting of, 6 repeats of a unit comprising:

A hydrophobic region (A) comprising, or consisting of, VGVAPGVGVLPG sequences (SEQ ID No: 10), A region (B) comprising or consisting of the sequence AAAKAAAKAAK (SEQ ID No: 3)

A hydrophobic domain (C) comprising, or consisting of, VGVAPGVGVLPG sequences (SEQ ID No: 10), and A domain (D) comprising, or consisting of, the sequence GGACLGKACGRKRK (SEQ ID No: 6).

According to this particular aspect, a polypeptide according to the invention is characterized by a size, expressed in molecular weight (kDa) which is close to, or of the same order of magnitude, as that of native trophoelastin, i.e. 72 KDa, and a basic isoelectric point, preferably very basic and close to the isoelectric point of the native tropoelastin, i.e. 10.4.

According to a still more particular aspect, the object of the invention is a synthetic polypeptide derived from tropoelastine, the amino acid sequence of which comprises or consists of the sequence SEQ ID No: 8. The polypeptide comprises an alternation of hydrophobic and crosslinking domains of tropoelastin, as well as its C-terminus region (domain 36) according to the following primary amino acid sequence: H$_2$N-[(VGVAPG-VGVLPG)$_6$-(AAAKAAA-KAAK)]$_6$-(VGVAPG-VGVLPG)$_6$-GGA-CLGKACGRKRK-COOH (SEQ ID No. 8).

According to another particular aspect, the object of the invention is a synthetic polypeptide derived from tropoelastine as defined above, in the form of a fusion protein, with a polypeptide-tag which may be easily identified and/or linked by a known ligand, especially during the production and purification of the polypeptide derived from tropoelastin, since the addition of the polypeptide tag does not alter the properties of the polypeptide derived from tropoelastin. Preferably, such a polypeptide tag has the following properties: low electrical charge, no influence on the structure of the polypeptide derived from elastin according to the invention, and especially chosen from the following polypeptides: Flag, poly-histidine, HA, GST, c-Myc, Glu-Glu, V5, biotin, S15. Those skilled in the art can readily choose a polypeptide tag from their general knowledge and publications available in the field. According to one particular aspect, a polypeptide according to the invention comprises, from its N-terminus to its C-terminus, a polypeptide tag and a polypeptide derived from tropoelastine. More particularly, a polypeptide according to the invention comprises, from its N-terminus to its C-terminus, an amino acid, in particular a cysteine or any other amino acid, a polypeptide tag and a polypeptide derived from tropoelastine.

According to a still more particular aspect, the object of the invention is a synthetic polypeptide derived from tropoelastine, the amino acid sequence of which comprises, or consists of, the sequence SEQ ID No: 9. This polypeptide comprises, from its N-terminus to its C-terminus, a cysteine, a polypeptide tag and a polypeptide derived from tropoelastin.

In another aspect, the object of the invention is an isolated nucleotide sequence encoding a polypeptide according to the invention.

According to a particular aspect, the object of the invention is an isolated nucleotide sequence comprising, or consisting of, the sequence SEQ ID No: 11 coding for the polypeptide according to the invention of sequence SEQ ID No: 8.

According to another particular aspect, the object of the invention is an isolated nucleotide sequence comprising, or consisting of, the sequence SEQ ID No: 12 coding for the polypeptide according to the invention of sequence SEQ ID No: 9.

According to another aspect, the object of the invention is a nucleotide vector comprising a nucleotide sequence coding for a polypeptide, according to the invention. By "vector" is meant a nucleic acid molecule capable of transporting a nucleotide sequence to which it is linked, or of allowing the expression of the protein encoded by a nucleotide sequence to which it is operably linked (expression vector).

According to a particular aspect, the object of the invention is a nucleotide vector comprising the sequence SEQ ID No: 11 coding for the polypeptide according to the invention of sequence SEQ ID No: 8.

According to another particular aspect, the object of the invention is a nucleotide vector comprising the sequence SEQ ID No: 12 coding for the polypeptide according to the invention of sequence SEQ ID No: 9.

The object of the present invention is a biocompatible material comprising a polypeptide according to the invention.

The object of the present invention is a biocompatible material comprising a polypeptide according to the invention, characterized in that the polypeptide is crosslinked. In other words, the polypeptide is self-assembled by covalent bonds.

The object of the present invention is a biocompatible material comprising a polypeptide according to the invention and a crosslinking agent.

The term "biocompatible material" according to the invention denotes a three-dimensional or crosslinked structure that can be accepted by a living being, in other words that is capable of fulfilling its function without adverse effect on the biological environment in which it is implanted. A biocompatible material according to the invention is preferably a hydrogel, i.e. a material comprising a solid component, consisting of a matrix of polypeptide chains optionally comprising polymer chains, and a liquid component constituted by a high proportion of water, an aqueous liquid or a biological fluid.

Preferably, a biocompatible material according to the invention is non-toxic and non-carcinogenic. Preferably, a biocompatible material according to the invention is biodegradable, or resorbable. The term "biodegradable" refers to the ability of a product to be degraded under the action of at least one living organism, wherein the appreciation of biodegradability takes into account the degree of decomposition and the time required to achieve this decomposition.

According to a first aspect, a biocompatible material according to the invention comprises at least one polypeptide according to the invention. According to another aspect, a biocompatible material according to the invention comprises at least one polypeptide according to the invention and a crosslinking agent.

According to a second aspect, a biocompatible material according to the invention comprises at least one polypeptide according to the invention and a polymer, preferably a hydrophilic polymer. According to another aspect, a biocompatible material according to the invention comprises at least one polypeptide according to the invention, a polymer, preferably a hydrophilic polymer, and a crosslinking agent.

The term "crosslinking agent" refers to an agent capable of creating bonds between the components to form a network structure or arrangement. In a biocompatible material according to the invention, the crosslinking agent is chosen from non-toxic and biocompatible agents.

According to the first aspect of a biocompatible material according to the invention, in which it comprises a polypeptide according to the invention and a crosslinking agent, the crosslinking agent may be an enzyme, a reactive chemical compound, or a conventional crosslinking reagent on primary amines. Such a crosslinking agent is preferably chosen from the group consisting of: aldehydes (such as glutaraldehyde), enzymes (transglutaminases, lysyls oxidases), natural crosslinking agents (genipin), or any homofunctional or heterofunctional agent whose reactive groups may be esters-activated aldehydes, carbodiimides, isothiocyanates, epoxides, photoactivatable groups. The spacer between the reactive groups is traditionally, but not exclusively, a polyethylene glycol chain or an aliphatic chain. According to a more particular aspect, a biomaterial according to the invention comprises a crosslinking agent preferably selected from the group consisting of: a natural crosslinking agent (genipin) or enzymes (lysyls oxidases, transglutaminases), or bifunctional agents based on polyethylene glycol (NHS-PEG-NHS), generally exhibiting low toxicity.

According to a second particular aspect, the object of the present invention is a biocompatible material comprising a polypeptide according to the invention and a hydrophilic polymer. According to this particular aspect, the hydrophilic polymer comprises reaction groups intended to allow the formation of covalent bonds with the polypeptide. For example, the polymer may comprise photosensitive groups (acrylic or methacrylic), wherein the crosslinking of the gel take place in the presence of the polypeptide, under the effect of a light source. According to another particular aspect, the polypeptide and the hydrophilic polymer are crosslinked by means of "click chemistry" type agents. The click chemistry, of the acetylenic-azido or thiol maleimide type, requires modification upstream of the polymer, wherein this modification is well known to those skilled in the art.

The term "hydrophilic" refers to the ability to create hydrogen bonds with water molecules. The term "hydrophilic polymer" refers to a polymer capable of creating many bonds with water molecules, and therefore comprises a high proportion of aqueous phase.

According to a second particular aspect, the object of the present invention is a biocompatible material comprising a polypeptide according to the invention, a crosslinking agent and a hydrophilic polymer.

In a biocompatible material according to the invention, the hydrophilic polymer and the crosslinking agent allow controlled crosslinking around the polypeptide according to the invention, it is not the non-specific adsorption of the polypeptide on the surface of a material. constituted by the crosslinked hydrophilic polymer.

According to another particular aspect, the object of the present invention is a biocompatible material comprising a polypeptide according to the invention, a crosslinking agent and a hydrophilic and branched polymer. The term "branched" is here equivalent to the term "arborescent" and refers to a polymer whose structure is not linear but is three-dimensional.

A polymer adapted to a biocompatible material according to the invention ideally has the following properties: standardized synthesis method, good synthesis yield, homogeneity, mechanical behavior adapted to biological activity, significant possibilities of chemical reactivity, biocompatibility, and allowing good adhesion of the cells.

According to a still more particular aspect, the object of the invention is a biocompatible material comprising a polypeptide according to the invention, a crosslinking agent and a hydrophilic polymer, wherein the hydrophilic polymer is preferably branched and chosen from lysine polymers, and especially from dendrimers of polylysine or other amine polymers of the polyethylene imines (PEI), polyamidoamines (PAMAM), keratins, chitosan.

For the purposes of the present invention, the term "polylysine dendrimers" means arborescent L-lysine polymers such as those described by Denkewalter et al (1981, 1983) and Rodriguez-Hernandez et al (2003) and Klok et al (2002) as well as those based on D- or L-lysine described in the international application WO2006/114528 and called polylysine grafted dendrimers (DGL). All of these dendrimers are either lysine only, with lysine being either in (D) or (L) form, or more than 30 mol % lysine and also containing units of other amino acids. In the case where the dendrimers consist solely of (D)-lysine or (L)-lysine, we speak of homopolylysine, in other cases we speak of heteropolylysines.

In an advantageous embodiment of the invention, native or modified polylysine grafting dendrimers (DGL) of generation 1 to 7 are used, preferably DGLs of generation 2, 3, 4 or 5, and more preferably DGLs of generation 3. In view of the very small size of the DGL-1 generation (DGL-1), the concentrations of DGL-1 to be used to obtain a hydrogel would lead to a material of greater rigidity than that of the material prepared from DGL generation 2 or 3, and therefore are of little interest for the invention, while dendrimers of generations greater than 7 tend to form aggregates that make it difficult to use.

The term "native polylysine grafted dendrimers" means dendrimers in which the amine functions are free. The term "modified polylysine grafted dendrimers" means dendrimers in which all or part of the amine functions are covalently or non-covalently bound to another amino acid, to electropositive chemical functions (quaternary amines, guanidine), to hydrophobic functions such as chains ($C_2$-$C_{18}$) alkyl, cholesterol functions, or poly-ethylene glycol. Those skilled in the art will be able to carry out the modifications of these amine groups using their general knowledge or the techniques described in the literature, such as those described by Rossi J. C. et al (2012). They will also be able to choose the type of modifications to be made depending on the biocompatible material to be synthesized.

According to a still more particular aspect, the object of the invention is a biocompatible material comprising a polypeptide according to the invention, a crosslinking agent and a hydrophilic polymer, wherein the hydrophilic polymer is a polylysine grafted dendrimer consisting solely of L-lysine, i.e. homopolymer of L-lysine, and which constitutes a polycationic framework, preferably arborescent.

According to a still more particular aspect, a polymer of a biocompatible material according to the invention is a polylysine grafted dendrimer prepared according to the method described in the international application published under the number WO 2006/114528. This polymer is scalable in size, depending on its level of generation, a specific mechanical behavior and biological activity that may be attributed to the different polymers according to their size.

Preferably, in a material according to the invention, the polylysine grafted dendrimer is a generation 3 dendrimer, prepared according to the method described in the international application published under number WO 2006/114528, with an average molecular weight of approximately 15,000 at about 30000 Da, preferably about 21500 Da, more preferably about 22000 Da, a polydispersity of about 1.4, and about 80 to about 170, in particular about 123 —$NH_2$ free external groups. This polylysine grafted dendrimer has the advantage of offering good synthesis yield, homogeneity, good mechanical behavior and good biological activity when it is crosslinked with a polypeptide according to the invention. It allows a high chemical reactivity by the presence of multiple primary amine functions. It is biocompatible and completely non-immunogenic, unlike nonlinear polylysine. It allows good adhesion and good spreading of the cells, causing very little differentiation and allowing activation of the transcription of a gene coding for a surface protein, the α5 sub-unit of integrins. In addition, it is stealthy with respect to the immune system, as it does not induce the production of antibodies directed against lysine dendrimers.

According to another particular aspect, the object of the invention is a biocompatible material according to the invention comprising a polypeptide according to the invention, a crosslinking agent and a hydrophilic polymer, in which the crosslinking agent is a homo-bifunctional or hetero-bifunctional agent.

According to a more particular aspect, a material according to the invention comprises a bifunctional crosslinking agent comprising a polyethylene glycol chain, of variable length, preferably between 200 Da and 20000 Da, preferably 2000 Da, functionalized at each of its ends by a group capable of interacting with the primary amine type functions, and, in particular, with the side chain of a lysine.

According to a more particular aspect, a material according to the invention comprises a bifunctional crosslinking agent, functionalized at each of its ends by an activated ester function, by 2-(N-Succinimidyl-succinylamino) ethyl (NHS), or by any other chemical function that is able to interact with primary amine functions.

According to a still more particular aspect, a material according to the invention comprises a crosslinking agent comprising a chain of PEG functionalized at each of its ends by an activated ester function, by 2-(N-succinimidyl-succinylamino) ethyl (PEG-NHS).

According to an even more particular aspect of the invention, the biocompatible material is characterized in that:
  the polypeptide comprises the amino acid sequence SEQ ID No: 8, and preferably comprises the sequence SEQ ID No: 9
  the polymer is a grafted dendrimer of polylysine of generation 3, and
  the crosslinking agent is bifunctional and comprises a polyethylene glycol (PEG) chain functionalized at each of its ends, preferably by an activated ester function, by 2-(N-succinimidyl-succinylamino) ethyl (PEG-NHS).

The third object of the present invention is a method for preparing a biocompatible material according to the invention, wherein the method comprises a step of mixing a polypeptide according to the invention and a crosslinking agent.

Those skilled in the art will readily determine, depending on the choice of the crosslinking agent, that it is of a chemical or enzymatic nature, with the reaction conditions necessary for the crosslinking to take place.

According to a particular aspect of a method according to the invention, the mixture of a polypeptide according to the invention and a crosslinking agent is produced under the following conditions:
  Concentration of crosslinking agent of at least 10 mM, and preferably of 50 mM, wherein the crosslinking agent is in particular genipin or an agent comprising a PEG chain functionalized at each of its ends by 2-(N-succinimidyl-succinylamino)ethyl (PEG-NHS or NHS-PEG-NHS).
  Concentration of the polypeptide according to the invention, of at least 1 mg/ml, preferably of between 1 and 100 mg/ml, and preferably of 50 mg/ml.
  Reaction medium consisting of a buffer, such as PBS (150 mM NaCl, pH 7.4),
  Temperature: for a genipin type agent: between 35 and 45° C., preferably between 36 and 44° C., preferably about 42° C., and preferably 42° C.; for a PEG-NHS type agent: between 4 and 45° C., preferably between 4 and 25° C., preferably 4° C.,
  Duration of reaction comprised between several minutes and several hours, wherein the reaction typically comprises a contacting phase of the polypeptide and the crosslinking agent, lasting between 5 and 20 minutes, and preferably about 15 minutes for a PEG-NHS type agent, or a duration of between 1 and 24 hours, and preferably 16 hours for a genipin-type agent, followed by washing, wherein the material obtained is then deposited in any solvent or a suitable solution, especially PBS at pH 7.4.
  Optionally, the material may be dried or lyophilized, and then hydrated in any suitable solvent or solution, especially PBS at pH 7.4.

The concentration of the different components makes it possible to modulate the different properties of the biocompatible material. The level of crosslinking agent makes it possible to vary the rigidity of the biomaterial, while the level of elastic polypeptide makes it possible to modulate the elastic component of the material.

The mixture of a polypeptide according to the invention and a crosslinking agent leads to the gelation of the assembly in order to generate an elastomer-type material, wherein an elastomer is defined as a polymer having elastic properties that is obtained after crosslinking. The gelation control makes it possible to manipulate the elements in the soluble state in order to impose a shape on the material. In addition, the concentration of the various components makes it possible to modulate the various properties of the crosslinked structures obtained by the implementation of the method. The level of elastic polypeptide makes it possible to modulate the elastic component of the structure. The preparation of the elastomers is generally carried out under very mild conditions, wherein gelation is carried out at ambient temperature and atmospheric pressure and the use of organic solvents is rarely required.

According to a still more particular aspect of a method according to the invention, a hydrogel is prepared by mixing a polypeptide according to the invention and a crosslinking agent in the presence of a hydrophilic polymer. According to another aspect of a method according to the invention, the mixture of a polypeptide according to the invention and a crosslinking agent is produced in the presence of a hydrophilic and branched polymer. The hydrophilic polymer is chosen, in particular, from: lysine polymers, polyethylenimines (PEI), polyamidoamines (PAMAM), keratins and chitosan. The preparation of the hydrogels is generally carried out under very mild conditions, wherein the gelation is carried out at ambient temperature and atmospheric pressure and the use of organic solvents is rarely required.

According to an even more particular aspect of a method according to the invention, the polymer is a grafted dendrimer of polylysine, preferably of generation 3, prepared according to the method described in the international application published under the number WO 2006/114528.

According to this particular aspect of a method according to the invention for the preparation of a biocompatible material, a polypeptide according to the invention and a hydrophilic polymer are mixed in the presence of a crosslinking agent, wherein the crosslinking agent is a bifunctional agent chosen from agents comprising a variable size chain functionalized at each of its ends by a group capable of interacting with the primary amine type functions, and, in particular, with the side chain of a lysine amino acid. According to this particular aspect of a method according to the invention, the crosslinking agent comprises a PEG chain functionalized at each of its ends by a ester function activated by 2-(N-succinimidyl-succinylamino)ethyl (PEG-NHS).

The mixture of a polypeptide according to the invention, a hydrophilic polymer and a crosslinking agent leads to the gelation of the assembly. According to a particular aspect, in a method according to the invention for the preparation of a biocompatible material, the mixture of a polypeptide according to the invention, a crosslinking agent and a polymer is produced under the following conditions:
- reaction time between 15 seconds and 10 minutes
- concentration of crosslinking agent of at least 20 mg/ml, and preferably between 50 and 100 mg/ml
- concentration of polypeptide according to the invention, of at least 0.1 mg/ml, preferably between 1 and 20 mg/ml, and preferably 3.75 mg/ml,
- polymer concentration of at least 25 mg/ml and preferably between 25 and 100 mg/ml.

The rate (or concentration) of crosslinking agent and polymer makes it possible to vary the stiffness of the biomaterial, while the rate (or concentration) of elastic polypeptide makes it possible to modulate the elastic component of the material.

According to another more particular aspect of a method according to the invention, the preparation of a biocompatible material comprises:
- a step of mixing a polypeptide according to the invention and a crosslinking agent, in the presence or absence of a hydrophilic polymer, in order to obtain a biocompatible material,
- a step of casting the biocompatible material in a mold of a definite shape.

The casting step makes it possible to impose the desired shape on the biomaterial.

According to another more particular aspect of a method according to the invention, the preparation of a biocompatible material further comprises a step of generating pores within the material, wherein the steps of pore generation and casting may be successive, in any order, or simultaneous.

The macro-environmental organization generated by the pore size makes it possible to use the biocompatible material as a guiding matrix for the cells or as a temporary filling matrix. The term "porosity" refers to the ratio of the void volume to the total volume of the material. Modular porosity may thus be achieved around custom-designed porogens and according to suitable methods. The pores of the gel allow the diffusion of nutrients towards the cells as well as that of the degradation products of the cellular metabolism towards the outside of the gel.

The pores within the material may be generated by any method known to those skilled in the art. According to a first aspect of the invention, the pores may be generated by any chemical or physical method known to those skilled in the art. According to one particular aspect, the biocompatible material may be mixed with a pore-forming material which will then be removed from the mixture, according to a method known to those skilled in the art, thereby generating a porous biocompatible material.

According to an even more particular aspect of a method according to the invention, the preparation of the biocompatible material comprises a step of casting the biocompatible material in a mold of a definite shape in the presence of a porogenic material, and a step of extraction, or withdrawal, of the porogenic material.

According to this aspect, the method allows the hydrogel to be crosslinked around temporary or pore-forming scaffolds, which will then be removed to make room for interconnected gaps through which cells may migrate freely. This formulation therefore allows the colonization of the hydrogel by resident cells (in vivo) or by isolated cells in the context of tissue reconstruction in vitro.

According to this particular aspect of the invention, the casting step of the biocompatible material in the presence of a porogenic material is carried out under conditions permitting the crosslinking of the biocompatible material around the porogenic material.

In a method according to the invention, the porogenic material is constituted by any suitable material, chosen, in particular, from linear or branched alkanes, and especially paraffin, and from aliphatic or aromatic polymers.

According to a particular aspect of a method according to the invention, the porogenic material consists of paraffin, preferably in the form of beads of calibrated size. The established porogen thus consists of a compact assembly of paraffin beads with calibrated dimensions, from 1 micron to 1 millimeter, preferably between 10 microns and 500 microns, preferably from 50 to 250 microns, in particular from 50 to 100 microns, from 100 microns to 180 microns, and from 180 to 250 microns. These compact assemblies are made by controlled fusion of the beads, by incubation at controlled temperatures and times, or by centrifugation. The extraction of paraffin is carried out by consecutive baths in boiling ethyl alcohol. This results in porous and interconnected structures. These different reaction conditions make it possible to finely modulate the structural properties of a material according to the invention (porosity, pore size, rate and size of interconnection between the pores).

The invention also relates to a method comprising casting a composite material in the presence of a porogenic material as defined above.

The invention therefore relates to a biocompatible material as obtained by the implementation of a method according to the invention, wherein the material resulting from the reaction between a polypeptide according to the invention and a crosslinking agent, according to a first aspect, or the material resulting from the reaction between a polypeptide according to the invention, a hydrophilic polymer and a crosslinking agent, according to a second aspect.

The fourth object of the present invention is an in vitro cell culture support comprising a biocompatible material obtained by a method according to the invention.

According to a more particular aspect, a cell culture support according to the invention comprises, or consists of, a biomaterial comprising a polypeptide according to the invention and a crosslinking agent.

In a more particular aspect, a cell culture support according to the invention comprises, or consists of, a biomaterial comprising a polypeptide according to the invention, a hydrophilic polymer and a crosslinking agent. According to this aspect, the polypeptide comprises the sequence SEQ ID No: 8 or SEQ ID No: 9 and/or the polymer is a polylysine grafted dendrimer of generation 3, obtained by a method described in WO 2006/114528 and/or the crosslinking agent is PEG-NSS. Preferably, according to this aspect, the culture support is porous.

The macro-environmental organization generated by the pore size makes it possible to use the crosslinked structure, in particular the hydrogel, as a guiding matrix for the cells or as a temporary filling matrix. The inventors have shown the cell penetration control capabilities as well as biocompatibility and bioresorption of a material according to the invention. In, the comparison of the colonization control by human fibroblasts of materials of different porosity shows that a single pore size (100-180 or 50-100 μm) offers a less pronounced cell colonization than a pore size mixture with a ratio of 50/50 or 75/25 (100-180 or 50-100, after 14 days.

According to a more particular aspect, the object of the invention is the use of a biocompatible material according to the invention, or obtained by a method according to the invention, as in vitro cell culture support, wherein the cells are possibly cells that are isolated or suspended in any type of medium, natural or synthetic, or cells comprised in a tissue or tissue fragment, or cell line cells or in a particular environment. In fact, this culture medium does not induce cell death, and allows the adhesion of any type of adherent cell.

A cell culture support according to the invention may be used to cultivate all types of eukaryotic cells, of human or animal origin, and preferably to cultivate cells chosen from the following group: skin cells, in particular the cells of the dermis, epidermis and/or hypodermis, keratinocytes, fibroblasts, in particular cutaneous fibroblasts, bone cells, chondrocytes, vascular wall cells, especially endothelial cells and smooth muscle cells, nerve cells, and any cells present in the soft tissues. A cell culture support according to the invention may also be used to culture stem cells, in particular pluripotent stem cells, multipotent stem cells, unipotent stem cells, as well as progenitor cells.

A cell culture support according to the invention may be inoculated by cells by any known means.

A cell culture support according to the invention may be used for any application in the field of the study of the matrix organization of cells and/or tissues, and in particular in the fields of pharmacology, toxicology and cosmetology.

The fifth object of the present invention is a biocompatible material according to the invention, or as obtained by a method according to the invention, for its use in humans or animals for tissue engineering or for stimulating tissue regeneration.

The object of the present invention is also a biocompatible material according to the invention, or as obtained by a method according to the invention, for its use in humans or animals for tissue engineering, and preferably for soft tissue engineering.

By "tissue engineering" is meant substitution, enhancement, induction and/or stimulation of tissue, as well as conditioning of multipotent cells prior to implantation. It is understood that the term "conditioning" is intended to bring the multipotent cells into contact with the biocompatible material, wherein the latter serves as a support or vehicle for the multipotent cells. The goal of tissue engineering is to synthesize, from matrices containing the necessary ingredients, a tissue replacing a damaged or missing tissue.

"Soft tissues" means tissues with elastic properties, and in particular, but not limited to, skin tissues, cardiovascular tissues, in particular heart valve tissues and/or blood vessels, nerve fibers, osteoarticular tissues, including ligamentous tissues, intervertebral discs and elastic cartilage, vocal folds.

Once implanted at the desired location of the host organism, the material must withstand the various mechanical stresses and maintain its volume for a sufficient duration, while transmitting these stresses to the encapsulated cells.

Ideally, in the case of tissue regeneration, it is desirable for the material to degrade spontaneously to give way to the formed tissue.

According to one particular aspect, the object of the invention is a biocompatible material according to the invention for the engineering of a soft tissue selected from the group of skin tissues, cardiovascular and nerve tissues, osteoarticular tissues, muscle tissue, vocal fold tissue.

Preferably, a biocompatible material according to the invention is characterized by mechanical and biological properties equivalent to those of the tissue for which it will be used. In particular, the elasticity of the material used, characterized, in particular, by its Young's modulus, should be compatible with, and preferably close to, the elasticity of the targeted tissue.

According to a particular aspect, the object of the invention is a biocompatible material for cutaneous cellular engineering, and, in particular, for the stimulation of cutaneous cicatrization.

According to a still more particular aspect, the object of the invention is a biocompatible material for stimulating cutaneous healing of subjects suffering from major burns and/or elderly subjects suffering from chronic wounds.

According to another particular aspect, the object of the invention is a biocompatible material for the treatment of a pathology relating to elastogenesis imperfecta or a pathology related to a defect of the connective tissue.

According to another particular aspect, the object of the invention is a biocompatible material for tissue filling, for cosmetological purposes or in reconstructive surgery, in particular following deep curettage following removal of a tumor or for the repair of vocal folds.

According to another particular aspect, the object of the invention is a biocompatible material according to the invention for stimulating bone reconstitution, for stimulating the regeneration and guiding of muscle fibers, for stimulating the synthesis of vascular fibers or for the replacement of blood vessels.

According to another particular aspect, the object of the invention is a biocompatible material according to the invention for the treatment of pathologies inducing hyper calcification or for stimulating the calcification of elastic tissues, in particular cardiovascular and osteoarticular tissues.

Finally, the object of the invention is a composite biomaterial comprising, or consisting of, a biocompatible material according to the invention and another compound, wherein the latter compound is constituted by a synthetic material, in particular a polymer, by a material of natural origin, or by a mixture of a synthetic material and a material of natural origin. In the case of a polymer, it is preferably a biodegradable polymer of synthetic or natural origin, chosen, in particular, from: polyesters, polyether, esters, polycoprolactone, collagen and cellulose. The compound may be in any suitable form, and especially in the form of fibers or nanofibers. According to a particular aspect, the composite biomaterial may comprise a biocompatible material according to the invention in combination with another compound, and it may, in particular, comprise a zone in which the biocompatible material according to the invention and the compound are associated, and, in the case of polymers, are co-polymerized.

The structure of the composite biomaterial should be appropriate for the envisaged application of the composite material, in a particular aspect this structure mimics that of an organ of the human or animal body, more particularly a blood vessel or a micro-blood vessel.

According to another aspect, the object of the invention is a method for preparing a composite biomaterial according to the invention, wherein the composite biomaterial comprises, or consists of, a biocompatible material according to the invention and another compound, wherein the method comprises a step of mixing a polypeptide according to the invention and a crosslinking agent, and a step of contacting the mixture with the compound. Those skilled in the art will readily determine, depending on the nature of the compound, the reaction conditions necessary for the crosslinking to take place and for the desired composite biomaterial to be obtained.

According to another aspect, the object of the invention is the use of a biocompatible material according to the invention for the preparation of a composite biomaterial comprising the biocompatible material and another compound, wherein the compound is constituted by a synthetic material, such as a polymer, a material of natural origin, or a mixture of synthetic materials and materials of natural origin.

Examples 1 to 7 and FIGS. 1 to 15 which follow illustrate the invention.

In example 1, FIG. 1 shows a schematic representation of a particular embodiment of a polypeptide according to the invention, according to which the polypeptide comprises, from its N-terminus to its C-terminus: a cysteine; a polypeptide-tag, represented by a rectangle; a first domain comprising the repeat of a unit, wherein the unit comprises a repeat hydrophobic region (A), represented by chevrons, and a crosslinking region (B), represented by a spiral; a second hydrophobic domain (C), represented by chevrons; and a domain (D) corresponding to the domain encoded by exon 36 of the gene coding for tropoelastin, represented by a curved line. The Elactiv polypeptide is one of the more particular embodiments of the invention, wherein its amino acid sequence, which corresponds to the sequence SEQ ID No: 9, is also shown in FIG. 1. The Elactiv polypeptide comprises, from its N-terminus to its C-terminus: a cysteine; Flag polypeptide-tag; a first domain comprising six repeats of one unit, wherein the unit comprises a hydrophobic region repeated 6 times, and a crosslinking region; a second hydrophobic domain repeated 6 times; and a domain corresponding to the domain encoded by exon 36 of the gene coding for tropoelastin.

Figure 2:
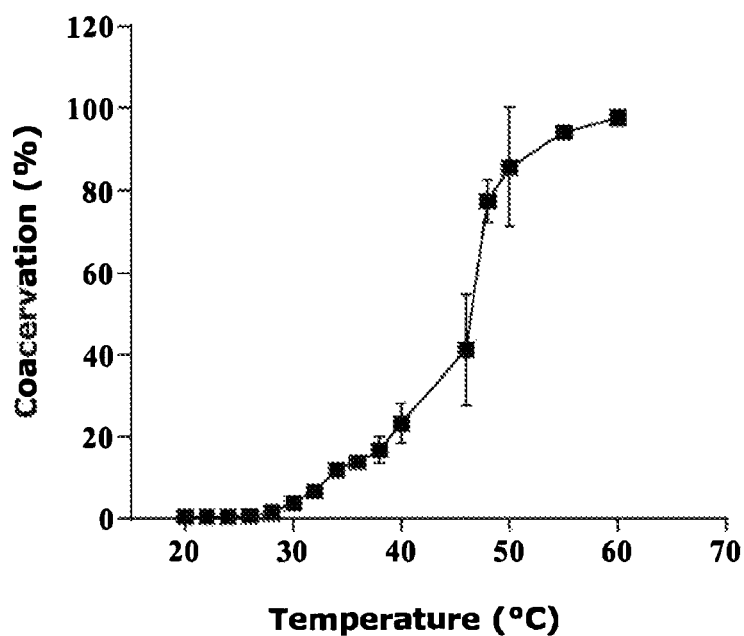
Figure 3:
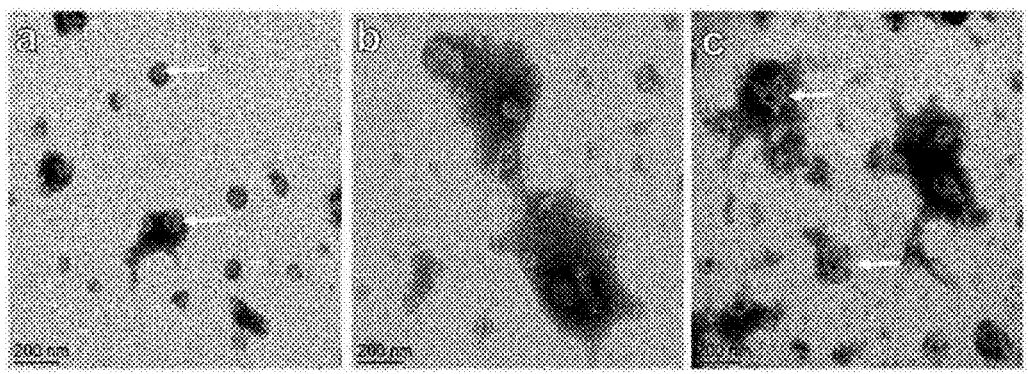
Figure 3:
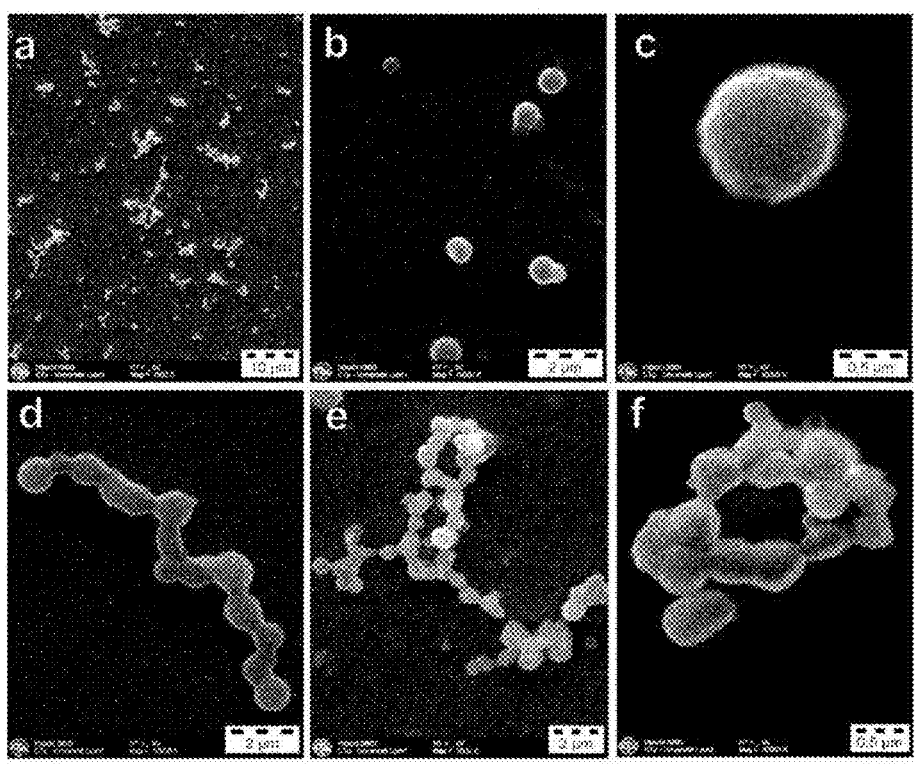
Figure 4:
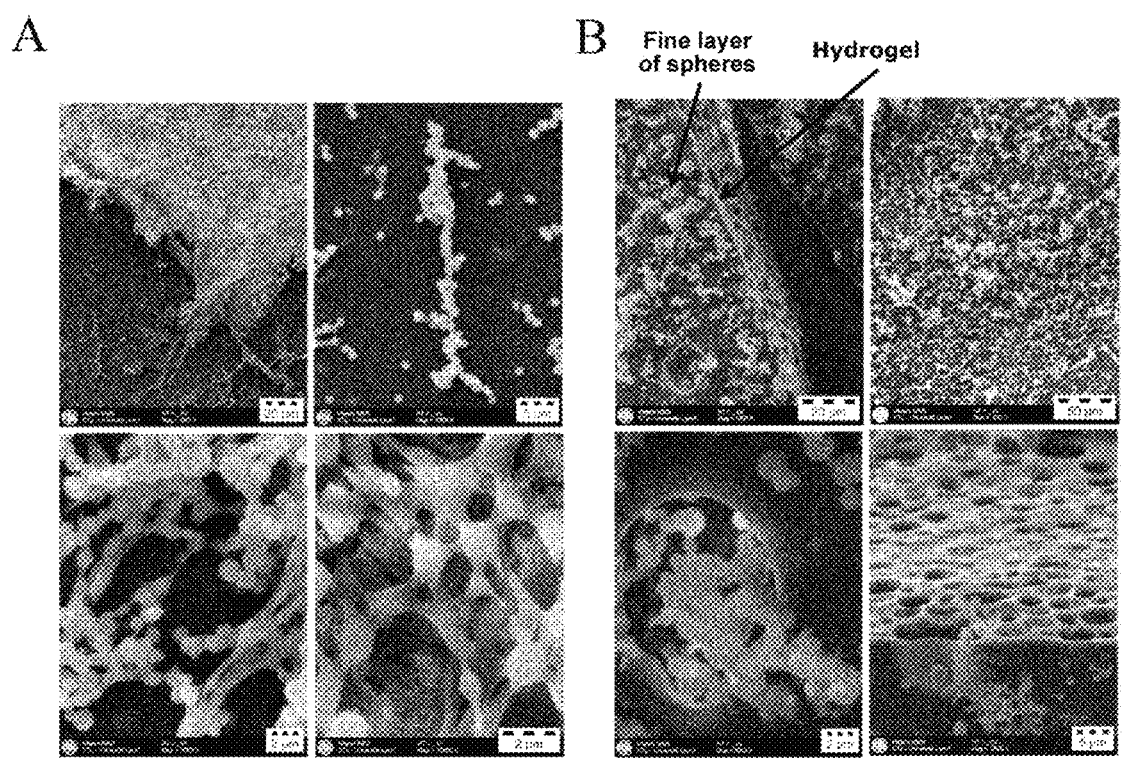
Figure 5:
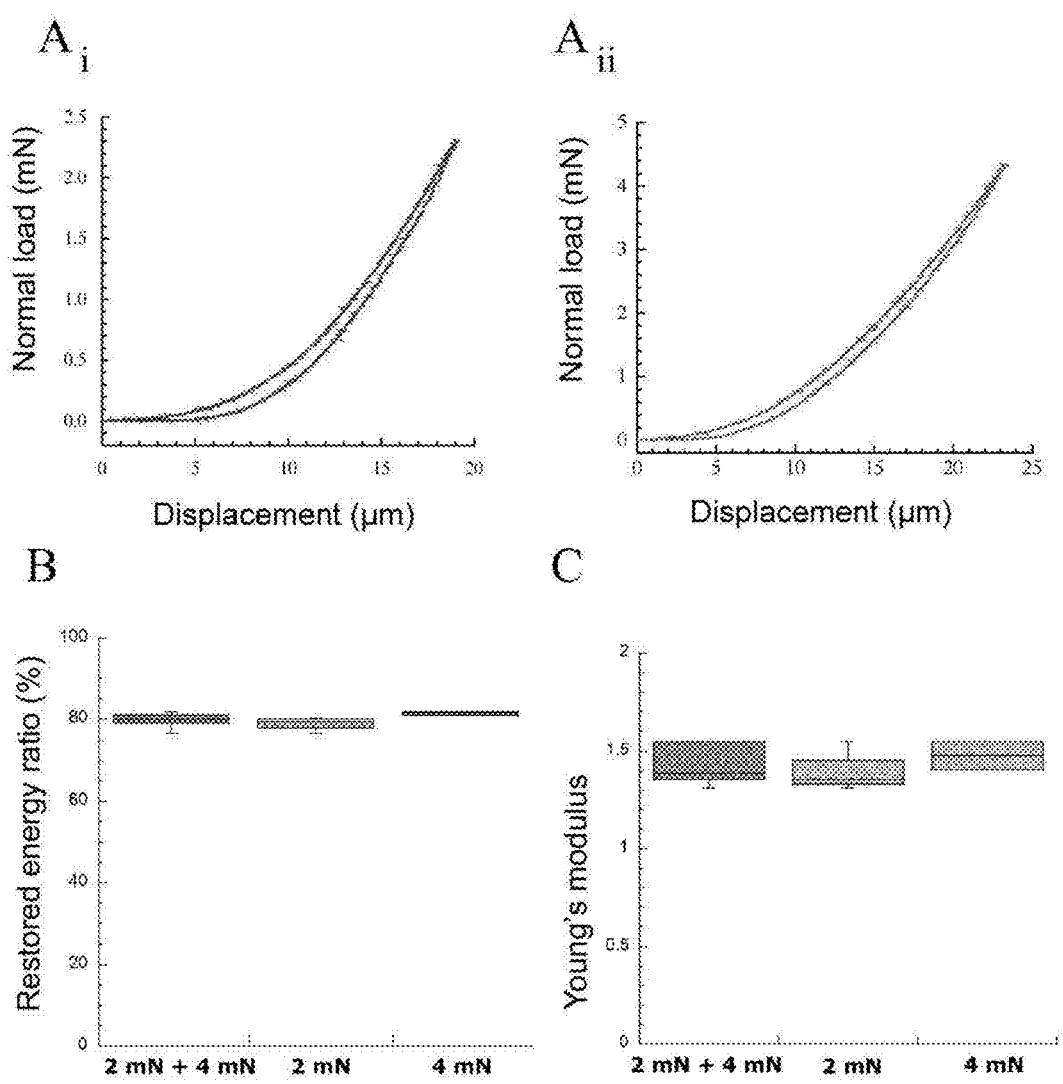

FIG. 2 shows the thermal characterization of the polypeptide and the coacervation profile of a solution of Elactiv' 1 mg/ml in PBS (pH 7.4) in the temperature range 20-60° C.

FIGS. 3A and 3B show the self-assembly of Elactiv' coacervates. FIG. 3A corresponds to the transmission electron image microscopies illustrating the coacervates formed from Elactiv' solutions at 120 µg/ml (a), 240 µg/ml (b) and 2 mg/ml (c) in PBS. (FIG. 3A). FIG. 3B corresponds to Elactiv' coacervate scanning electron microscopy images formed from a solution of Elactiv' at 2 mg/ml in PBS and illustrating a set of structures (a), monomers (b and c), and coalescing spheres (df).

FIGS. 4A and 4B correspond to scanning electron microscopy images illustrating Elactiv' structures formed from 2 mg/ml Elactiv' solutions containing 50 mM genipin (FIG. 4A) and formed from solutions of 50 mg/ml Elactiv' containing 50 mM genipin (FIG. 4B).

FIGS. 5A, 5B and 5C show the result of indentation tests on genipin-crosslinked Elactiv' hydrogels with a normal applied load of 2 mN (FIG. 5Ai) or 4 mN (FIG. 5Aii), the energy restored by the Elactiv' hydrogel after the indentation test with a normal load of 2 mN and 4 mN on a hydrogel (FIG. 5B) and the Young's modulus (MPa) of the Elactiv' hydrogel defined according to the normal load applied to the sample during the test (FIG. 5C).

Figure 6:
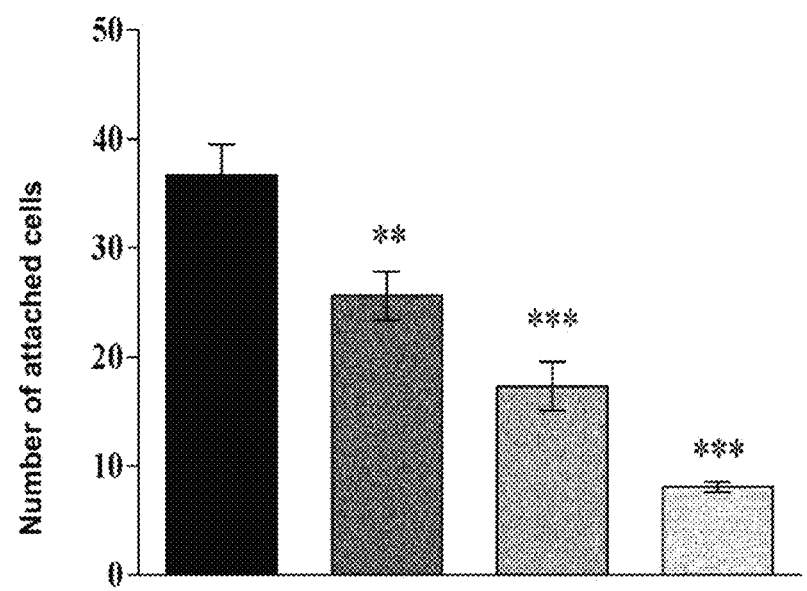
Figure 7:
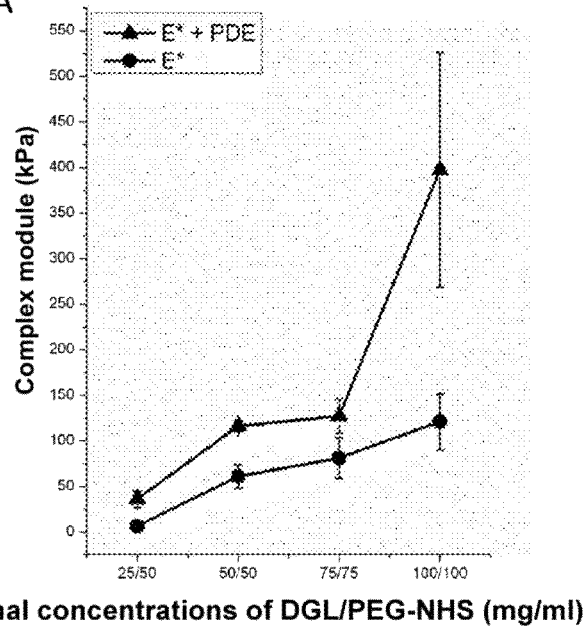
Figure 7:
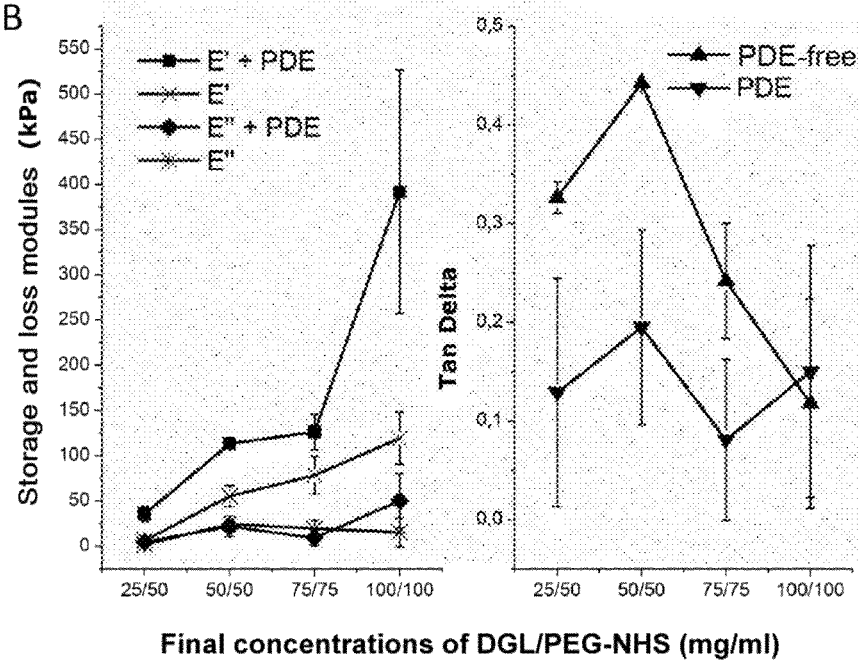

In Example 2, FIG. 6 shows the number of adherent cells on a surface coated with Elactiv' in the presence or absence of anti-integrin antibodies $\alpha_v\beta_3$ and L-Lactose.

In example 3, FIG. 7A represents the complex modulus (E*) of hydrogels of various DGL/PEG-NHS compositions, expressed as a ratio of concentrations in mg/ml, in the presence (●) or absence (▲) of PDE at 3.75 mg/ml. FIG. 7B represents the storage modulus (E') in the presence (■) or absence (X) of PDE at 3.75 mg/ml, and the loss (E') in the presence (●) or absence (*) of PDE at 3.75 mg/ml, and tan delta hydrogels of various DGL/PEG-NHS compositions, expressed as a ratio of concentrations in mg/ml, in the presence (▼) or absence (▲) of PDE at 3.75 mg/ml.

Figure 8:
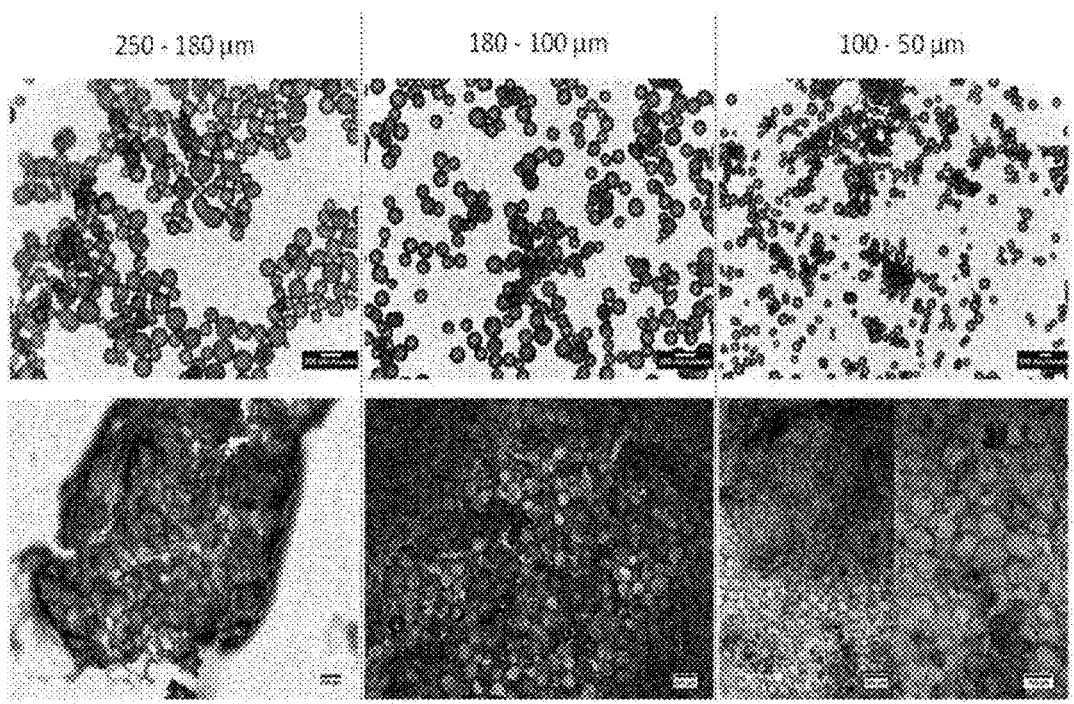

FIG. 8 shows paraffin beads of different particle size (top row: 250-180 microns, 180-100 microns and 100-50 microns respectively) and resulting porous hydrogels stained with coomassie blue (bottom row).

Figure 9:
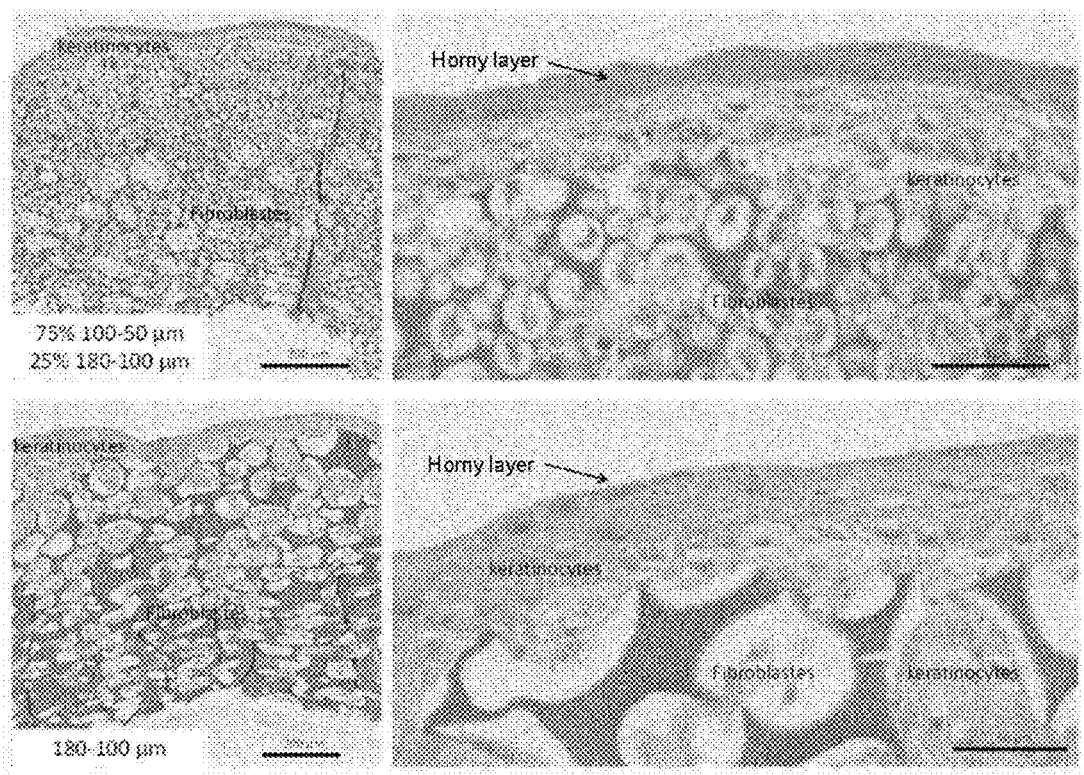

In example 5, FIG. 9 represents reconstructed skins obtained with hydrogels (DGUPEG-NHS 50/50 mg/ml) of different porosities: 75% 100-50 µm/25% 180-100 µm (top of the figure), and 100% 180-100 µm (bottom of the figure). The fibroblasts colonized the pores of the hydrogel and the keratinocytes formed a stratum corneum on the surface.

Figure 10:
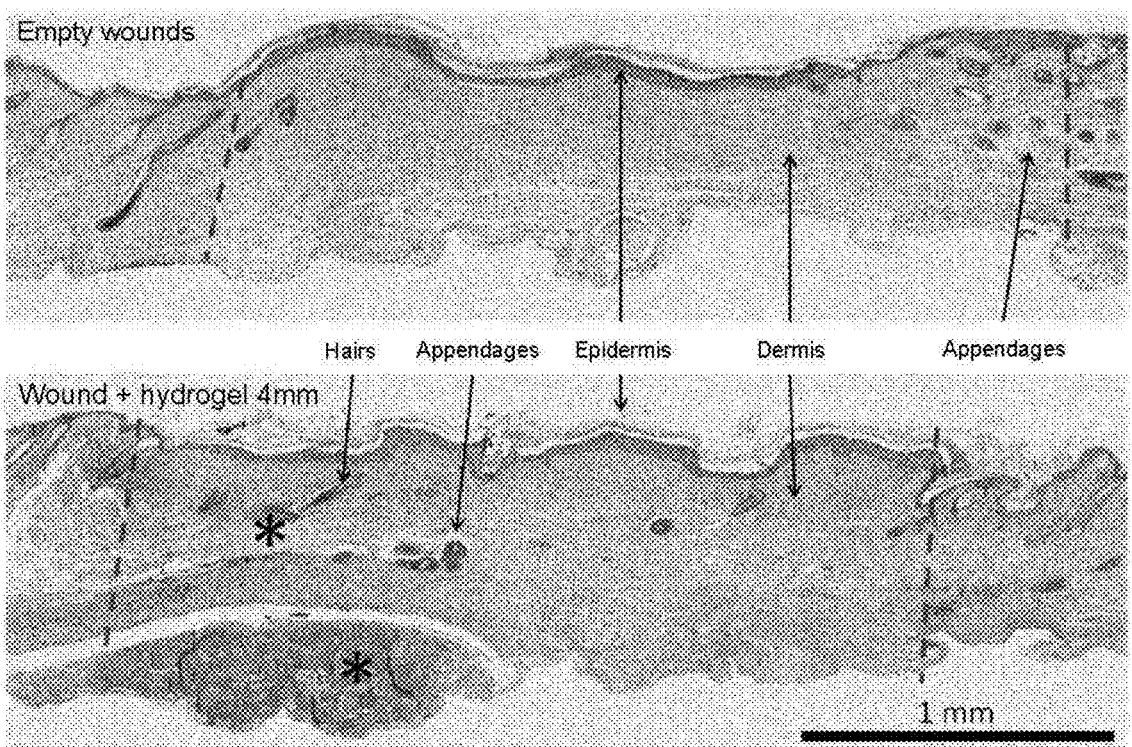

FIG. 10 shows the healing of skin wounds after 2 weeks, wherein the wounds are left empty (top of the figure) or filled with porous hydrogels (DGL/PEG-NHS 50/50 mg/ml, containing 0.875 mg/ml of PDE) (180-100 µm) 4 mm thick (bottom of the figure). The hydrogels (black asterisk) are fully invaded by cells and appear fragmented within the original wound (dotted line).

Figures 11A, 11B, 11C:
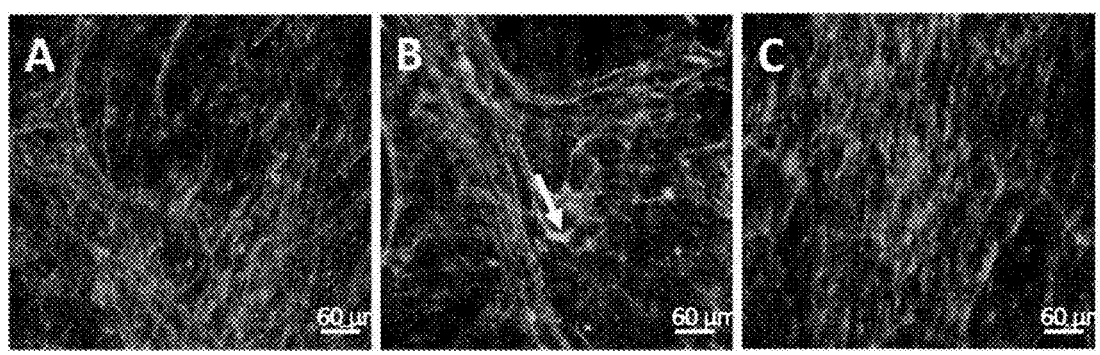

In Example 6, FIGS. 11A and 11B show a tubular hydrogel/nanofiber composite biomaterial; FIG. 11A schematically shows the structure of the composite biomaterial which comprises, during its synthesis and from the center to the periphery: a glass central rod, a nanofiber layer, a mixture of hydrogel and nanofibers and then the glass tube used for molding the composite biomaterial. The three photographs (from left to right) of FIG. 11B indicate: a composite tube of internal diameter 1 mm and external diameter 2 mm, a magnification of this tube, and an electron micrograph of nanofibers.

FIG. 12A to 12D show composite nanofiber/hydrogel tubes characterized by the following values:

| | Total diameter of the nanofiber tube | Internal diameter of the hydrogel tube: | External diameter of the hydrogel tube |
|---|---|---|---|
| 12A | 1 mm | 1 mm | 2 mm |
| 12B | 1 mm | 1 mm | 3 mm |
| 12C | 2 mm | 2 mm | 3 mm |
| 12D | 2 mm | 2 mm | 3 mm |

In example 7, FIGS. 13A and 13B show histograms showing the measurement of the external diameters (FIG. 13A) and internal diameters (FIG. 13B) with, on the ordinate, the value given by the experimental measurement by image analysis under two angles of rotation: 0° (left bars) and 90° (right bars) and on the abscissa, the theoretical value of these diameters.

FIGS. 14A, 14B and 14C show the incorporation of the polypeptide according to the invention into fibrillar elastin deposits in dermal fibroblast cultures. FIGS. 14A and 14B respectively show fluorescence imaging at 8 days after confluence (J8) of untreated dermal fibroblasts (FIG. 14A) or treated at 5 days after confluence (J5) with 1 µg/ml of polypeptide-rhodamine (FIG. 14B). FIG. 14C shows the effect of the addition of β-aminopropionitrile (β-APN) (lysyl oxidase inhibitor) to 350 μM. Tropoelastin is detected using an anti-tropoelastin antibody. The nuclei are counter-stained with 4,6-diamidino-2-phenylindole or DAPI. Scale bars=60 μm.

FIGS. 15A, 15B and 15C show the incorporation of the wild-type or mutated polypeptide into fibrillar elastin deposits in dermal fibroblast cultures using fluorescence imaging at 8 days post-confluence (J8) of treated dermal fibroblasts at 5 days after confluence (J5) with 1 μg/ml of rhodamine-polypeptide. Three versions of the polypeptide were tested: wild-type (FIG. 15A), mutated form on the RKRK motif (SEQ ID No: 5)>RKPR (SEQ ID No: 22) (FIG. 15B), and mutated form at the C>G disulfide bridge (FIG. 15C). Tropoelastin is detected using an anti-tropoelastin antibody. The nuclei are counterstained with DAPI. Scale bars=100 μm.

EXAMPLE 1 PREPARATION AND MECHANICAL CHARACTERIZATION OF THE POLYPEPTIDE

Material and Methods

The Elactiv' polypeptide has been designed to conform to the unique structure of human tropoelastin. It comprises alternating hydrophobic and crosslinking domains of tropoelastin, as well as its C-terminus region (domain 36) according to the following primary amino acid sequence: $H_2N$-C-DYKDDDDK-[(VGVAPG-VGVLPG)$_6$-(AAAKA-AKAAK)]$_6$-(VGVAPG-VGVLPG)$_6$-GGACLGKACGR-KRK-COOH (SEQ ID No: 9).

The gene encoding for Elactiv' was designed to conform to the unique structure of human tropoelastin. It encodes a protein identified by an alternation of hydrophobic and tropoelastin crosslinking domains, as well as its C-terminus region (domain 36) according to the following primary amino acid sequence: $H_2N$-C-DYKDDDDK-[(VGVAPG-VGVLPG$_6$-(AAAKAAAKAAK)]$_6$-(VGVAPG-VGVLP-G)$_6$-GGACLGKACGRKRK-COOH (SEQ ID No: 9). The synthesis of the gene coding for Elactiv' was entrusted to the company GenScript (Piscataway, United States). The DNA sequence (1794 bp) was optimized for expression in prokaryotic E. coli system (SEQ ID No: 12).

For the construction of the pET30a-Elactiv' expression vector, the gene coding for Elactiv' was cloned into the prokaryotic expression vector pET30a, between the NdeI and SalI sites. To do this, the vector pET30a was digested with the restriction endonucleases NdeI, SalI (Promega, Charbonnières-les-Bains, France) and the resulting linearized vector was stored and purified. The NdeI/SalI fragment of Elactiv' and the linearized vector were ligated using T4 DNA ligase (Promega) by incubation overnight at 4° C. The recombinant vector pET30a-Elactiv' was amplified in competent JM109 bacteria, as previously described, then isolated using the Endofree Plasmid Maxi kit (Qiagen, Courtaboeuf, France). Digestion of the recombinant vectors with the restriction enzyme EcoRV made it possible to validate the purification of the plasmid before sequencing. The pET30a-Elactiv' vector was stored at −20° C.

The expression of Elactiv' was carried out as follows: the recombinant vector pET30a-Elactiv was used to transform BL21 competent bacteria (DE3) (Life Technologies, Saint-Aubin, France). The transformed bacteria were inoculated on Luria-Broth (LB)/agar plates containing 50 μg/ml of kanamycin (Sigma-Aldrich, Saint-Quentin-Fallavier, France). A single colony was used to inoculate 5 ml of LB containing 50 μg/ml kanamycin overnight at 37° C. with constant stirring. The culture was diluted 1:100 and the expression of Elactiv' was induced during the exponential phase of growth by the addition of 1 mM isopropyl-β-D-thiogalactopyranoside (IPTG) (Sigma-Aldrich) for 4 h at 30° C. with constant stirring. The bacteria were then harvested by centrifugation (10,000 g for 10 min at 4° C.) and the resulting cell pellet frozen overnight at −80° C. The bacteria were resuspended in 50 mM pH 8 Tris-HCl buffer and incubated 45 min at 80° C. After incubation for 1 h in ice, the soluble and insoluble fractions were harvested by centrifugation (15,000 g, 20 min at 4° C.) and analyzed on a sodium blue polyacrylamide-dodecyl sulphate gel (SDS-PAGE), colored coomassie blue G-250. This protocol resulted in about 20 mg of Elactiv' per liter of culture, assayed using the Quant-iT protein assay kit (Life Technologies).

The Elactiv' protein was purified from the soluble lysate of E. coli by a reverse transition temperature (Tt) method, as previously reported [Yeo et al, 2011]. The purification method involves at least one repeated cycle of solubilization of Elactiv' in phosphate buffered saline (PBS) at 4° C., followed by precipitation and centrifugation at 42° C. The purity of Elactiv' was evaluated by visualization on sodium dodecyl sulphate polyacrylamide gel (SDS-PAGE) stained with silver nitrate. The purified Elactiv' is passed through a 0.2 μm filter to ensure sterility, and stored at −80° C. until further use.

The biochemical characterization of Elactiv' was carried out as follows: the theoretical molecular weight (Mw) and the isoelectric point (pI) of Elactiv' were calculated from its primary amino acid sequence (Vector NTI Advance 11, Life technologies). Mass spectrometry by Electron Transfer Dissociation (ETD) was performed by the Protein Science Facility (PSF) platform (Institute of Protein Biology and Chemistry, Lyon, France) to confirm the presence of the disulfide bond in the C-terminus (domain 36) region of Elactiv'. For this, fragmentation of the [579-594] peptide was generated in ETD mode, using tandem mass spectrometry with liquid chromatography (LC-MS/MS).

The far-UV circular Dichroism (DC) spectra of Elactiv' and recombinant human tropoelastin (hTE) (Sigma-Aldrich) were recorded with a Chirascan spectrometer (Applied Photophysics, Leatherhead, UK) calibrated with the 1S-(+)-10-camphosulfonic acid. Measurements were made from 20° C. to 60° C. in a quartz cuvette 0.1 cm long (Hellma, Müllheim, Germany), with concentrations of Elactiv' and hTE at about 0.2 mg·ml$^{-1}$ in PBS pH 7.4. The spectra were measured in a wavelength window of 180 nm to 260 nm. Spectra were processed with Chirascan software to correct and smooth the baseline. The spectral units were expressed as mean molar ellipticity per residue.

The coacervation of Elactiv' and the size of the aggregates in solution were measured by dynamic light scattering (DLS) using a Malvern-DLS Zatasizer Nano S ZEN1600 (Malvern Instrument) device, for a temperature range of 20° C. and 60° C., with a stabilization time of 5 min. The Elactiv' samples were prepared at 1 mg/ml in PBS at pH 7.4. Eleven tests were carried out per sample to determine the size of the particle aggregates, in order to obtain a final average value at a constant temperature.

For observation by transmission electron microscopy, Elactiv' was dissolved at different concentrations (from 120 μg/ml to 2 mg/ml) in cold PBS (4° C.). All solutions were equilibrated at 42° C. for 15 min to induce coacervation. A formvar-carbon grid (Electron Microscopy Sciences, Hatfield, UK) was deposited on one drop of each sample at 42°

C. After 2 minutes, the excess solutions on the grid were transferred and the adsorbed samples were fixed with a 2% glutaraldehyde solution for 2 min at 42° C. The samples were washed three times with distilled water, and stained for 10 seconds with 2% phosphorous tungstic acid at pH 7 (1M KOH) and air dried. The observations were made with a Philips CM120 transmission electron microscope, equipped with a CDD digital camera (Gatan), at the Technical Center for Microstructures (University Lyon 1).

For scanning electron microscopy, a cold genipin solution (Sigma-Aldrich) was added to similar solutions of Elactiv' at 4° C. (2 mg/ml in PBS) to reach a final concentration of 2 and 50 mM. All solutions were equilibrated at 42° C. for 15 minutes to facilitate coacervation and crosslinking, then spread on glass slides (Braunschweig, Germany), and air dried at 42° C. for 15 min. The resulting slides were then washed several times in PBS prior to dehydration in gradual (50% to 100%) ethanol solutions. The samples were then soaked in 100% hexamethyldisilazane for 3 minutes and transferred to a desiccator for at least 2 hours to avoid contamination of the water and to evaporate the residual solvent. All the samples were mounted on aluminum heels and sprayed with a thin layer (~3 nm) of copper (Bal-tec MED 020, Leica Microsystems SAS, Nanterre, France). Imaging was carried out using a Hitachi S800 FEG scanning electron microscope at the Technical Center for Microstructures (University Lyon 1).

Genipin-crosslinked Elactiv' hydrogels were prepared as follows: Purified Elactiv' was dissolved in PBS (150 mM NaCl, pH 7.4) to a final concentration of 50 mg·ml$^{-1}$, at 4° C. The sample was coacerved at 42° C. and pelleted by centrifugation at 300 g in 1.5 ml flat-bottom microcentrifuge tubes to a height of 1 mm. The pellet was covered with 200 µl of 50 mM genipin (Sigma-Aldrich) and crosslinked overnight at 42° C. The gel was recovered and rehydrated in PBS pH 7.4.

The mechanical properties of Elactiv' were determined, in particular, using an original device of low load indentation, based on the technique previously developed for biological tissues in vivo and in vitro (Pailler-Mattei et al, 2013). The indentation test consists of recording the penetration depth of a rigid indenter according to the normal load applied, during a loading/unloading experiment. In this study, indentation tests are performed in controlled displacement mode. Z displacement is obtained from the National Instrument displacement table, and controlled by a displacement sensor. The maximum displacement during the loading/unloading cycle can reach about 500 µm with a resolution of 1 µm. The experimental setup offers a wide range of indentation rates from 1 to 100 µm·s$^{-1}$.

In the present study, two different normal charges were applied, $F_z$=2 mN and $F_z$=4 mN, for a constant indentation rate V=20 µm·s$^{-1}$. The indenter used was a spherical steel indenter, with a radius of curvature R=1.6 mm. There was no waiting period between loading and unloading and only one loading cycle was performed for each test. The indentation tests were repeated five times on the Elactiv' sample. The sample was deposited in a glass crystallizer for testing. The indentation tests are carried out by total immersion in physiological saline to avoid or minimize the adhesion effect due to capillary phenomena between the sample and the indenter.

Results

Synthesis:

Elactiv' was designed to conform to the unique structure of human tropoelastin. It comprises alternating hydrophobic domains (VGVAPG-VGVLPG) and crosslinking domains (AAAKAAAKAAK) corresponding to highly conserved motifs among the species, as well as a C-terminus region (domain 36) comprising a disulfide bridge and a positively-charged sequence RKRK (SEQ ID No: 5). This domain is recognized as facilitating the self-assembly of tropoelastin and its incorporation into elastic fibers. Furthermore, a Flag octapeptide was added to the N-terminus region to facilitate the detection of Elactiv' without affecting the overall structure of the protein or its biological activity (FIG. 1). The gene coding for Elactiv' was cloned into the prokaryotic expression vector pET30a. The recombinant vector pET30a-Elactiv' was used to transform competent E. coli BL21 (DE3) bacteria. The bacteria were stimulated with 1 mM IPTG to induce Elactiv' expression. After SDS-PAGE analysis, Elactiv' was detected in the soluble and insoluble cell fractions of the bacterial lysate with an apparent molecular weight of about 55 kDa. The results are compared for induced and uninduced cultures. Purification of Elactiv' was done from soluble E. coli lysate by successive reverse transition cycles (ITC), as previously reported (Yeo et al, 2011). The samples were analyzed by SDS-PAGE and the gel was stained with silver nitrate. Elactiv' could be formally identified by western-blot using an anti-FLAG antibody.

Physicochemical Characterization of Elactiv'

Elactiv' has a theoretical molecular weight of 50.6 kDa and a very basic isoelectric point of 10.31, of the same order of magnitude as human tropoelastin (10.4). LC-MS/MS analyzed by ETD confirmed the presence of the disulfide bridge in the C-terminus region.

Circular dichroism (CD) was used to determine the secondary structures of Elactiv' in comparison with recombinant human tropoelastin (hTE). The spectra were recorded in a solution of PBS at 20, 40 and 60° C., for a concentration of 0.2 mg/ml. At 20° C., the Elactiv' and hTE profiles are characterized by a negative peak at 198 nm and a negative shoulder less than 220 nm, suggesting a left helix polyproline II (PPII) conformation, although the shoulder is less pronounced in Elactiv'. By increasing the temperature from 20 to 60° C., the peak is slightly shifted towards red, in particular for Elactiv', resulting from a decrease in the stability of the PPII helix.

Thermal Characterization

The thermal profile revealed that the coacervation of an Elactiv' solution in PBS begins to appear when the temperature reaches 30° C., corresponding to the transition temperature (Tt), and a maximum coacervation was obtained at 60° C. (FIG. 2). FIG. 2 shows the coacervation profile of a solution of Elactiv' 1 mg/ml in PBS (pH 7.4) in the temperature range 20-60° C. The variation of the turbidity of the solution at each temperature is expressed as a percentage of a maximum. On the other hand, DLS analysis confirmed a variation in the size of suspended Elactiv' aggregates which increases above temperature-dependent Tt, causing a sharp increase in turbidity (Table 1).

TABLE 1

| | Temperature (° C.) | | |
|---|---|---|---|
| | 20 | 60 | 20 |
| Size (nm) | 62.8 | $1.3 \cdot 10^4$ | 81.9 |

The size of these aggregates ranges from 60 nm (20° C.) to 1104 nm at 60° C. When the Elactiv' solution is cooled again to 20° C., the aggregates recover a size of 80 nm, of the same order as the initial condition demonstrating the reversibility of the phenomenon. The results are expressed by the mean±ESM of 3 replicates.

Self-Assembly of Elactiv's Molecules

To further study the aggregation properties of Elactiv', solutions of 120 µg to 2 mg/ml were prepared in PBS and heated to a temperature (42° C.) above the transition temperature to induce coacervation. Elactiv' was then visualized by negative staining in transmission electron microscopy (TEM) at 120 µg/ml, Elactiv' forms small individual spheres of low internal electron density (white arrows in the figure) very likely indicating hollow spheres (FIG. 3aa). From 240 µg/ml, the spheres do not remain individualized, but begin to fuse and form aggregates up to 200 nm in diameter (FIG. 3Ab). At 2 mg/ml, the aggregates show a higher external electron density due to the fusion of the individual Elactiv' spheres (white arrows in FIG. 3Ac). This fusion is also observable by scanning electron microscopy of Elastiv' coacervates formed from different structures of Elactiv' (3Ba), monomers (3Bb-c) and coalescent spheres (3Bd-f) formed with Elactiv' in PBS. The edges of the spheres are not regular (FIG. 3Bc). In addition to being organized in the spheres, on a larger scale, the spheres merge together and connect like beads on a chain (FIG. 3Bd), thus forming various geometric shapes (FIG. 3Be-Bf).

Crosslinking of Elactiv' Structures

When observed by scanning electron microscopy, in the presence of 50 mM genipin, aggregates of Elactiv' (at 2 mg/ml in PBS) form a very dense network of these structures forming fibers (FIG. 4A), with diameters similar to those of elastic fibers in vivo. The interconnection of these fibrilar assemblies also reveals new empty structures comparable to pores. When the concentration of Elactiv' is increased to 50 mg/ml with 50 mM genipin, most of the Elactiv' spheres have already coalesced to form a porous structure, but a small amount of isolated spheres may still be observed on the surface of the network, as well as inside the pores (FIG. 4B).

Mechanical Properties of Elactiv'

To study the mechanical properties, indentation tests were carried out from previously crosslinked 3D structures. The indentation curves were recorded by total immersion in PBS with a normal applied load of 2 mN (FIG. 5Ai) or 4 mN (FIG. 5Aii), for a constant penetration rate V=20 µm s⁻¹.

The indentation tests make it possible to determine a reduced Young's modulus $E^*$ of the Elactiv' lattice, from the measurement of the normal contact stiffness, $k_z$, corresponding to the slope of the initial part of the discharge curve. For a volume material in contact with a rigid axial symmetry penetrator, the normal stiffness is related to the reduced Young's modulus by [35]:

$$E^* = \frac{\sqrt{\pi}}{2} \frac{K_z}{\sqrt{A}}$$

wherein A is the projected contact area. $E^*$ is defined as follows:

$$\frac{1}{E^*} = \frac{1-v_1^2}{E_1} + \frac{1-v_2^2}{E_2},$$

wherein $E_1$, $v_1$ and $E_2$, $v_2$ are respectively Young's modulus and the Poisson ratio of the indenter and the Elactiv' structure. In this study, given that $E_1$ (steel)<<$E_2$ (Elactiv'), it may be considered that $E^*$ is the reduction of the apparent Young's modulus of the Elactiv' structure, $$\frac{1}{E^*} = \frac{1-v_1^2}{E_1}.$$

The energy analysis of the indentation curve makes it possible to estimate the energy ratio restored by the Elactiv' structure during the unloading phase. The ratio of the restored energy has been noted and defined as follows:

$$\psi = \frac{\int_{z_{max}}^{0} F_z|_{unloading} \, dz}{\int_{0}^{z_{max}} F_z|_{inloading} \, dz} \times 100$$

wherein $F_z|$loading is the normal load variation during loading, and $F_z|$unloading which is the normal load variation during unloading; $Z_{max}$ is the maximum penetration depth.

The results indicate that in the normal load range used, the structure of Elactiv' exhibits the same mechanical behavior: The reduced Young's modulus of the structure is between 1.4 MPa and 1.5 MPa (FIG. 5C, Young's modulus (MPa) of the Elactiv' hydrogel defined according to the normal load applied to the sample during the test) regardless of the normal load used. The ratio of the restored energy is approximately 80% (FIG. 5B, energy restored by the Elactiv' hydrogel after the indentation test with a normal charge of 2 mN and 4 mN on a hydrogel).

EXAMPLE 2: CHARACTERIZATION OF THE CELLULAR RESPONSES TO THE POLYPEPTIDE

Materials and Methods

For cell culture, normal human dermal fibroblasts (NHDF) isolated from juvenile prepuce (Promocell, Heidelberg, Germany) were cultured at 37° C., 5% $CO_2$ in complete medium: DMEM/F-12 ratio 1:1 (Invitrogen, Cergy Pontoise, France) supplemented with 10% fetal calf serum (FCS) (Sigma-Aldrich), 100 µg/ml penicillin and 0.1 mg/ml streptomycin (Sigma-Aldrich). The cells were seeded in 100×20 mm Optilux plates (BD Biosciences Labware, Brumath, France) at a minimum density of 4000 cells cm⁻² for the subculture. The cells were used after a limited number of subcultures (passage 5-6).

The CyQuant Cell Proliferation Assay Kit (Molecular Probes, Invitrogen, Saint-Aubin, France) was used together with a microplate reader (Infinite® M1000 microplate reader PRO Tecan, Männedorf, Switzerland) to evaluate the effect of Elactiv' on the viability (in homogeneous phase) and the proliferation (in heterogeneous phase) of NHDF.

Before the proliferation assay, the microplates were adsorbed at 10 µg/ml in PBS for 2 h at 4° C. with Elactiv', hTE (Sigma-Aldrich), collagen I (Gibco, Invitrogen) or bovine albumin. (BSA fraction V, Euromedex, Souffelweyersheim, France). The plates were then washed three times with PBS. For the tests, the cells were seeded at a density of 6000 cells/cm² and incubated overnight in complete medium to allow cell adhesion. For viability tests, various concentrations of Elactiv' or VGVAPG (SEQ ID NO: 19) elastin peptide (GenScript) diluted in complete medium were added 24 hours after cell seeding. Viability and proliferation were monitored for 10 days. The culture media were refreshed every 2 days and for each downtime, the medium was removed and the plates frozen at −80° C. before analysis according to the manufacturer's recommendations.

Cell adhesion was measured as follows: Elactiv' was adsorbed on the surface of Millicell EZ 8-well glass slides (Millipore Merck) at 10 µg/ml in PBS at room temperature for 2 hours, then slides were washed three times in PBS. Confluent NHDFs were harvested by incubation with 1 mM EDTA at 37° C. for 5 min. The cell suspension was centrifuged at 300 g for 5 min and the cell pellet was resuspended in 1 ml of serum-free medium. Cell density was adjusted to $4 \times 10^4$ cells/ml in fibroblast growth medium (PromoCell). Before inoculation, the cells were pre-incubated for 45 min with an $\alpha_v\beta_3$ integrin-blocking antibody (clone LM609, Merck Millipore, Saint-Quentin en Yvelines, France) at 20 µg/ml and/or in the presence of L-lactose 10 mM (Euromedex). The cells were then inoculated for 90 minutes on the previously functionalized slides. The medium was aspirated and the wells were gently rinsed once with PBS. Cells were fixed with paraformaldehyde (Sigma-Aldrich) 4% (v/v) for 20 minutes and rinsed 3 times with PBS. Hoechst (Sigma-Aldrich) and phalloidin-TRITC (Sigma-Aldrich) was added to the cells at 1 µg/ml in PBS for 15 min at room temperature. The cells were rinsed 3 times with PBS and the slides were mounted with Permafluor solution (LabVision, Thermo-Scientific, Illkirch, France). The cells were visualized by fluorescence microscopy with an Axioplan Imaging microscope (Carl Zeiss, Le Pecq, France) and photos were taken on a Coolsnap fx camera (Photometrics, Tucson, Ariz., USA) for quantification of the cells.

To measure the kinetics of the degradation by the MMP-12 protein, the recombinant human MMP-12 was diluted to 50 µg/ml in test buffer (50 mM Tris, 10 mM $CaCl_2$), 150 mM NaCl, Brij 0.05% (w/v) of pH 7.5) and activated by addition of p-aminophenylmercuric acetate (Calbiochem, Molsheim, France) to a final concentration of 1 mM at 37° C. for 4 hours. 1 µg of Elactiv' or hTE was incubated at 30° C. in the presence of 5 µg/ml activated MMP-12 alone or in combination with 10 mM EDTA (negative control inhibiting MMP activity). After 0, 15, 30, 60 and 120 minutes, the reactions were stopped by adding 10 mM EDTA. The ability of MMP-12 to degrade Elactiv' and hTE was assessed by Western-Blot analysis using an anti-alpha elastin antibody (ab21607, Abcam, Paris, France).

Results

The biocompatibility of Elactiv' was evaluated in the presence of normal human dermal fibroblasts (NHDFs) by cell proliferation assays (quantification of DNA) either in homogeneous phase (in solution) or in heterogeneous phase (surface functionalization).

In solution, the polypeptide is dispersed directly in the cell culture medium in a concentration range of 0.1 to 10 µg/ml. For surface functionalization, it is the absorption of the polypeptide on the surface of the cell culture plates. The adsorption is carried out at 10 µg/ml in PBS for 2 h at 4° C. The plate is then rinsed 3 times with PBS before seeding the cells.

In a first experiment, the NHDFs were incubated for 2 to 10 days in a homogeneous phase with medium alone or supplemented with Elactiv' or with the peptide of elastin VGVAPG (SEQ ID NO:19) at 1 µg/ml and 10 µg/ml. The results are presented as: mean±EMS of triplicates. An ANOVA test followed by a Bonferroni post-test was performed for the determination of p (*p<0.05) values. As regards proliferation in the homogeneous phase, a significant increase in cell proliferation was observed 10 days after seeding with 10 µg/ml Elactiv', similarly to the elastin peptide VGVAPG (SEQ ID NO:19).

Heterogeneous phase cell proliferation was also determined for 10 days on surfaces coated with Elactiv' or control matrix proteins. The NHDFs were incubated for 2 to 10 days in heterogeneous phase on different substrates (untreated, BSA, collagen, VGVAPG peptide (SEQ ID NO:19) or Elactiv'). The result is expressed as the average of 4 replicates (mean±ESM). No change in fibroblast proliferation was observed under these culture conditions.

To know whether the C-terminus motif GRKRK (SEQ ID NO: 20) and the VGVAPG (SEQ ID NO:19) motif within Elactiv', respectively known to bind to the integrin $\alpha_v\beta_3$ and the EBP in human tropoelastin, are capable of inducing cellular attachment, the adhesion of NHDFs to an Elactiv' coating was studied with anti-integrin $\alpha_v\beta_3$ blocking antibody and/or in the presence of L-lactose, an EBP inhibitor (FIG. 6). The inhibition of NHDFs on a gel at 10 µg/ml of Elactiv' in the presence or absence of an $\alpha_v\beta_3$ integrin antibody and/or L-lactose is shown. The antibody LM609 (anti-$\alpha_v\beta_3$) and L-lactose are used at concentrations of 20 µg/ml and 3.6 mg/ml, respectively. The result is the average of duplicates (±ESM), wherein the statistical significance was evaluated with regard to the negative control (without anti-integrin antibodies $\alpha_v\beta_3$ or L-lactose), by an ANOVA one-way test followed by a Bonferroni post-test. The statistical results are presented as follows: P<0.01, * P<0.001.

In the presence of anti-integrin antibodies $\alpha_v\beta_3$ alone, the adhesion of the cells was inhibited by 30% while the supplementation of the culture medium with L-lactose gave rise to a 50% inhibition. Finally, when the two inhibitors were added simultaneously to the culture medium, the adhesion of the NHDFs was inhibited by 78%.

To determine the sensitivity of Elactiv' to be degraded by matrix metalloproteinases (MMPs), the kinetics of degradation by rhMMP-12, MMP recognized to cleave at least 86 sites of tropoelastin in vitro, including the VGVAPG (SEQ ID NO:19) motif, was performed and analyzed western-blot using an anti-alpha elastin antibody. The results show that Elactiv' is progressively degraded by MMP-12, but to a lesser extent than human tropoelastin.

EXAMPLE 3: CHARACTERIZATION OF ELASTINO-MIMETIC HYDROGELS

Materials and Methods

The third-generation lysine dendrigrafts (DGL) were prepared according to the method described in international application WO2006/114528 by Colcom (Montpellier, France). O,O'-Bis[2-(N-Succinimidyl-succinylamino)ethyl] polyethylene glycol (PEG-NHS, Mn 2000), polyvinyl alcohol (PVA, Mw 13000-23000), the Live/Dead Cell Double Staining Kit, penicillin and streptomycin, phalloidin, 2-(4-Amidinophenyl)-6-indolecarbamidine dihydrochloride, 4',6-Diamidino-2-phenylindole dihydrochloride (DAPI), para-formaldehyde, dimethyl formamide (DMF) and absolute ethanol were purchased from Sigma Aldrich (St. Louis, Mo., USA). Paraffin was purchased from Histolab products AB (Vastra Frolunda, Sweden). Phosphate buffer (PBS) is marketed by Thermo Fisher Scientific (Waltham, Mass., USA). The sieves of different sizes were purchased from the Villeurbanne glassworks (Villeurbanne, France). The optiskin film is manufactured by Urgo.

To form the hydrogel, a solution of DGL at different concentrations of PBS, with or without PDE at different concentrations, is mixed with a solution of crosslinking agent (PEG-NHS) at different concentrations of PBS or DMF. To form 100 µl of hydrogel, 37.5 µl of PBS containing PDE or not are added to 50 µl of DGL solution and mixed by vortexing. This solution is placed on ice and 12.5 µl of PEG-NHS solution is added and mixed by vortexing. The resulting crosslinking of the gel occurs under static conditions at room temperature.

The paraffin beads of different particle sizes are prepared by emulsification. 150 ml of a 0.5% (w/v) PVA solution in water are heated to 70° C. in a 200 ml beaker. In parallel, 5 g of paraffin flakes are melted in a beaker while ensuring that there is no boiling. While maintaining the temperature at 70° C., strong magnetic stirring takes place in the PVA solution and the liquid paraffin is poured into it. After 15 minutes, the hot paraffin emulsion in the PVA solution is poured into a cold (ice) water bath to instantly solidify the paraffin. The whole is then filtered successively with sieves of 250 µm, 180 µm, 100 µm and 50 µm. The paraffin beads are recovered and dried with the lyophilizer and then stored at 4° C.

The porous gels are formed by pore-forming approaches by crosslinking the hydrogel around and within a stack of paraffin beads of controlled particle size. To form 100 µl of porous gel, 100 mg of paraffin beads are deposited in a 2 mL microtube. The beads are packed at the bottom of the tube by mechanical action and by centrifugation (benchtop centrifuge, 2000 g, 15 seconds). If it is a mixture of beads of different particle sizes, it must first be mixed by inversion and vortexing. Before adding the hydrogel, the microtube is placed on ice. Then, 100 µl of hydrogel before crosslinking is deposited on the surface of the stack of paraffin beads in the microtube and immediately centrifuged at 2000 g for 2 seconds in order to make the gel penetrate between the paraffin beads. The composite containing the gel and paraffin beads is then left for crosslinking under static conditions at room temperature.

After 2 hours, the paraffin is extracted from the hydrogel by three successive baths of 1 hour in 300 ml of boiling absolute ethanol. The gels are then immersed in pure water for 10 minutes and then in PBS and stored at 4° C.

The mechanical properties of the hydrogel were measured by dynamic mechanical analysis (DMA 3100, Bose ElectroForce, USA). Hydrogel discs of diameter 12 mm and thickness 2 mm are sinusoidally compressed by an amplitude of 10%, after pre-compression of 10%, at a frequency ranging from 1 to 100 Hz, at room temperature. The force/displacement curves obtained make it possible to define the complex elasticity modulus (E*), as well as the complex storage (E') and loss (E") module and their ratio (tan delta) for each frequency. Each hydrogel composition is measured in triplicate.

Results

Characterization of Hydrogels

Elastomimetic hydrogels are formed by the combination of three components. The action of a crosslinking agent (PEG-NHS) on lysine dendrigrafts (DGL) and elastin-derived protein (PDE) allows efficient crosslinking and hydrogel formation. Crosslinking occurs through the formation of amide covalent bonds between the N-hydroxysuccinimine (NHS) functions of the crosslinking agent and the free amine functions of DGL and PDE. The crosslinking takes place rapidly (between 15 seconds and ten minutes) and under many conditions of concentration. The final concentrations of PEG-NHS and DGLs control the formation of the hydrogel as well as its rate of crosslinking (Table 2). Hydrogels are formed from a final concentration (in the hydrogel) of PEG-NHS at 50 mg/ml and DGL at 25 mg/ml. The presence of the PDE in the mixture does not seem to induce differences in the capacity or the crosslinking times.

TABLE 2

Hydrogel formation rate as a function of the final concentrations of PEG-NHS and DGL

| | | DGL (mg/ml) | | |
| --- | --- | --- | --- | --- |
| | | 25 | 50 | 100 |
| PEG-NHS (mg/ml) | 50 | 10 minutes | 30 seconds | |
| | 100 | | | 15 seconds |

The mechanical properties of the hydrogels are also affected by the final concentrations of the various constituents. As illustrated in FIG. 7A, the E* complex module of the PDE-free gels may be varied between 7 and 121 kPa by increasing the concentrations of DGL and PEG-NHS between respectively 25-100 mg/ml and 50-100 mg/ml. The presence of PDE in the hydrogel (3.75 mg/ml) results in the increase of E* for each combination of the other constituents (E* if between 36 and 397 kPa), indicating better compressive strength of the material. The mechanical behavior of the hydrogels is characterized by a storage modulus E' that is higher than the loss modulus E", which demonstrates an elastic behavior (FIG. 7B). This behavior is improved by the presence of the PDE in the hydrogel, as indicated by the decrease in tan delta (and therefore the energy dissipation) in the presence of PDE. This increase of the storage modulus in the presence of the protein tends to demonstrate that the DPE retains its intrinsic elastic properties within the hydrogel and transmits them to the hydrogel.

Porous Hydrogels

By a porogenic approach, pores of varying sizes may be incorporated within the hydrogels. Paraffin beads fractionated by sieving populations of different diameters can provide a scaffold around which the hydrogel may be crosslinked. The controlled particle size of the paraffin beads, especially from 250 to 180 microns, from 180 to 100 microns or from 100 to 50 microns, has made it possible to modulate the size of the pores formed after extraction of the paraffin (FIG. 8). Interconnected pores, of controlled size between 50 and 180 microns, allow cellular infiltration. By varying the ratio of pore diameters, cells may reach a depth of 1250 microns, with 80% of cells invading an average of 350 microns, within 14 days.

EXAMPLE 4: CYTOCOMPATIBILITY OF THE HYDROGELS IN VITRO

Materials and Methods

The cytotoxicity of the hydrogels was evaluated by live/dead fluorescent staining by culturing human foreskin fibroblasts on dense hydrogel discs 8 mm in diameter and about 0.5 mm in thickness. Morphology and cell proliferation were observed by labeling using fluorescent phalloidin. Before cell culture, the hydrogels are sanitized in a 70% ethanol bath for 12 hours before being rinsed three times for 10 minutes in PBS. The cells are seeded at a density of 5000 cells per hydrogel and cultured in DMEM-F12 (10% fetal calf serum, penicillin 100U/ml, streptomycin 100 µg/ml) for 8 days at 37° C. in an atmosphere containing 5% of $CO_2$. After 1, 5 and 8 days, phalloidin labeling is performed to visualize the actin cytoskeleton, while live/dead labeling is performed after 5 days in order to highlight the dead cells (in red) and living cells (in green).

The ability of cells to invade and colonize porous hydrogels was evaluated after culturing human foreskin fibroblasts deposited on the surface of porous hydrogel discs (6 mm in diameter, 2-3 mm thick) previously sanitized. An amount of 100,000 cells, in a volume of 10 µl, is seeded on the surface of the hydrogel discs. After 2 hours of cell adhesion at 37° C., the hydrogels are covered with culture medium (DMEM-F12, 10% fetal calf serum, penicillin 100U/ml, streptomycin 100 µg/ml) and cultured for 14 days in duplicates.

After 1, 7 and 14 days, the discs are fixed in paraformaldehyde (PFA, 4%) and fine sections of 8 µm are made by cryotomy. The cell nuclei are then labeled with DAPI and observed by fluorescence microscopy. Cellular penetration is quantified by image analysis using J-image and expressed as a distance from the cell seeding surface. 9 images of sections are analyzed for each hydrogel in duplicate, i.e. 18 images per hydrogel composition. The results of the image analyses are compared statistically by non-parametric tests (Kruskal-Wallis followed by the post-hoc test of Nemenyu).

Results

Cyto-Compatibility of the Hydrogels

In order to determine the ability of the hydrogels to allow adhesion and cell proliferation, human fibroblasts were seeded on dense gels of composition DGL/PEG-NHS 50/50 mg/ml, containing or not PDE (5.625 mg/ml). The observation of the morphology and the proliferation of human fibroblasts on the surface of hydrogels containing or not containing PDE, at 1, 8 or 12 days show that after one day, the cells adhere to the surface of the gels and about half acquires a fusiform phenotype characteristic of fibroblastic cells. The cells proliferate on the surface of the hydrogels and reach confluence after 8 days of culture. The presence of the PDE does not induce a significant difference in cellular behavior. The suitability and safety of the hydrogels for cell culture are also indicated by the low mortality observed after 5 days of culture on the hydrogels by live/dead test, in which the cytotoxicity of the hydrogels is evaluated, wherein the living cells are indicated in green and dead cells in red.

Porous Hydrogels as a Cell Substrate

The formation of porosity within the hydrogels allows the cells to penetrate in order to ensure colonization of the material and effective tissue formation. To validate this hypothesis, human fibroblasts were seeded on the surface of porous hydrogels of the same composition (DGL/PEG-NHS 50/50 mg/ml) but of different porosities, and cultured for 14 days. The variation in porosity can be obtained by mixing paraffin beads with a particle size of 180-100 µm and 100-50 µm at different mass ratios. During culture, the cells enter the porous hydrogels, as visualized by DAPI cuts and markings of the cell nuclei, confirming the interconnection of the pores. This interconnection may be connected to the prior stacking of the paraffin particles by centrifugation before association with the hydrogel, which makes it possible to ensure the contact between the beads and their compaction. After 14 days of culture, the various porosities all show a significant cellular invasion of up to 1250 µm in depth, as indicated on histograms of cell penetration obtained by image analysis and statistical analysis of the maximum penetrations reached by the cells in the hydrogels of different porosities. A statistical analysis of the cell penetration histograms indicates that if after 1 day the cells penetrated deeper into the 180-100 µm porosity and 25/75% 100-50/180-100 µm hydrogels, they reach a statistically greater maximum depth. important for mass ratios 50/50% 100-50/180-100 µm and 75/25% 100-50/180-100 µm ($p<0.05$).

EXAMPLE 5: USE OF POROUS HYDROGELS FOR SKIN HEALING

Materials and Methods

The possibility for porous hydrogels to integrate a skin wound and modify the healing method has been evaluated in wound models in mice. Two circular cutaneous defects of 8 mm were made on the back of C57BL6 mice using a biopsy punch to take only the cutaneous part without causing muscle damage. A silicone ring with an internal diameter of 8 mm and an outer diameter of 16 mm is glued and sutured around the wound before filling it with hydrogel discs (8 mm in diameter) of composition DGL/PEG-NHS 50/50 mg/ml containing 0.875 mg/ml PDE, 180-100 µm porosity and thicknesses 1 and 4 mm. The filled/empty wound and the silicone ring are then covered with an optiskin film for 7 days. Daily observation of the wounds is performed and closure of the wound photographed. After 14 days, the mice are euthanized, healed wounds are explanted, fixed in 4% PFA, embedded in paraffin, cut into sections of 8 µm and stained with hematoxylin-eosin-saffron.

Results

Biocompatibility of the Hydrogels In Vivo

The subcutaneous implantation of the hydrogels in the mouse for three weeks made it possible to show the biocompatibility of the dense and porous hydrogels, as observed after Masson trichome staining, which indicates the collagen in turquoise blue. A fibrous capsule, typical of the classical foreign body reaction, is present around all implanted hydrogels. In contrast to dense hydrogels, porous hydrogels exhibit a large centripetal cellular invasion that confirms the interconnection of pores, with diameters of 180-100 µm and 100-50 µm. The majority of cells invading empty pores are of a macrophagic morphotype. Their phagocytosis activity may be observed on the hydrogel, either at the hydrogel membranes between the pores or at the periphery of the dense hydrogels. Beyond macrophages, fibroblastic cells are also present in porous hydrogels and a collagenous matrix deposition is observed in the pores to a significant depth (1 mm). In addition, many blood vessels have invaded porous hydrogels, explaining the significant presence of macrophages and cell survival at significant depths in hydrogels. The presence of PDE (3.75 mg/ml) in dense or porous hydrogels does not appear to induce any significant cellular, vascular or inflammatory difference.

In all the conditions tested (dense hydrogel, porous, with or without the presence of PDE), it is important to note that the inflammatory response induced by the hydrogels is absent or very weak. In fact, no granulocyte or lymphocyte were detected.

Conclusion: The subcutaneous implantation of a biomaterial according to the invention for three weeks shows a significant cellular invasion and the bioresorption of the material, while the inflammation and the peri-implantation fibrous response appear weak.

Use of Porous Hydrogels for Skin Reconstruction

The strong cell colonization observed in vitro and in vivo suggests the suitability of porous hydrogels for three-dimensional cell culture and for their use as a complex tissue-forming medium. To evaluate this possibility, reconstructed skins were made by successively cultivating fibroblasts and human keratinocytes respectively within and on the surface of porous hydrogels of different porosities.

As indicated by FIG. 9, the fibroblasts colonized hydrogels, whether for a porosity of 75% 100-50 µm/25% 180-100 µm, or a porosity of 180-100 µm. The keratinocytes deposited on the surface of the gels, after proliferation of the fibroblasts, form a pluristratified structure characteristic of the epithelia. The deepest layer is formed by cohesive cells with a nucleus in the basal position. As it moves towards the surface, the diameter of the cells decreases and the nuclei tend to flatten and disappear in the outermost layer assimilated to a horny layer. As a whole, this structure is close to the natural epidermal structure of the skin. It should be noted, however, that 180-100 µm porosity hydrogels allow some keratinocytes to penetrate the pores close to the surface of the hydrogels, preventing the formation of a homogeneous basal layer. Our hypothesis is that under these conditions, the basal lamina on which the proliferative keratinocytes are in principle sitting is discontinuous. A modification of the fibroblast and keratinocyte seeding protocol could lead to more homogeneous ab initio colonization and more definite epidermal structures.

Integration of Hydrogels into the Cutaneous Wound and Potential Utility.

The biocompatibility, vascularization, cell colonization and deposition capacity of MECs, as well as the versatile elastic nature of hydrogels, make them attractive candidates for integrating with different types of wounds and for guiding healing. To evaluate this potential, hydrogels (DGL/PEG-NHS 50/50 mg/ml, containing 0.875 mg/ml of PDE) porous (180-100 µm) were deposited in cutaneous wounds made in mice. After two weeks of healing, the hydrogels of thickness 1 and 4 mm are present in the healed tissue (FIG. 10). They are fragmented and fully cellularized. In comparison with the wound left empty, the hydrogels seem to improve the scar tissue, notably by the presence of cutaneous appendages and hair in the dermis, some of which are in direct contact with hydrogel fragments. There are no significant differences in the epidermis between empty wounds or those filled with hydrogels, all of which show thickening.

EXAMPLE 6: COMPLEXATION IN PRE-ELASTIC FIBERS OF THE POLYPEPTIDE ACCORDING TO THE INVENTION AND MUTED POLYPEPTIDES

Materials and Methods

For cell culture, normal human dermal fibroblasts (NHDF) isolated from juvenile prepuce (Promocell, Heidelberg, Germany) were cultured at 37° C., 5% $CO_2$ in complete medium: DMEM/F-12 ratio 1:1 (Invitrogen, Cergy Pontoise, France) supplemented with 10% fetal calf serum (FCS) (Sigma-Aldrich), 100 µg/ml penicillin and 0.1 mg/ml streptomycin (Sigma-Aldrich). The cells were seeded at a density of 8,000 cells/m² on the surface of 12 mm diameter round glass coverslips in 24-well plate wells. The culture medium is replaced every two days until 8 days post-confluence. At the indicated times, the wild-type polypeptide (Elactiv') or its mutated forms were added to the culture medium at the concentration of 1 µg/ml for 3 days. The lysyl oxidase inhibitor, β-aminopropionitrile, was added simultaneously to the polypeptide at a concentration of 350 µM.

The mutations of the gene coding for the polypeptide were carried out using the QuickChange II directed mutagenesis kit (Agilent Technologies, Les Ulis) according to the supplier's recommendations from the expression plasmid comprising the wild-type gene (SEQ ID No: 12). The mutation on the sequence encoding the RKRK motif (SEQ ID No: 5) of the D domain was obtained using the following primers:

(SEQ ID NO: 15)
sense:
5'-aagcctgtggccgtaaacCTaGgtaagtcgacaagcttgc;

(SEQ ID NO: 16)
antisense
5'-gcaagcttgtcgacttacCtAGgtttacggccacaggctt.

The mutation on the codon corresponding to the first cysteine of the domain D, was obtained by using the following primers:

(SEQ ID NO: 17)
sense
5'-gcgtttacggccaccggctttacccaggc;

(SEQ ID NO: 18)
antisense
5'-gcctgggtaaagccggtggccgtaaacgc.

The productions and purifications of the mutant proteins were carried out in a manner similar to the wild-type protein. The fluorescent labels of each of the polypeptides were made by conjugation of tetramethylrhodamine-5-maleimide (Sigma-Aldrich). The polypeptides and the fluorescent agent were mixed in phosphate buffered saline (PBS) at concentrations of 2 mg/ml and 10 mg/ml respectively. After overnight incubation at room temperature in the dark, labeled polypeptides were purified by ITC to remove excess fluorescent agent At the end of the culture, immunofluorescent staining of tropoelastin and nuclei was performed. The culture medium was aspirated and the wells were rinsed three times with PBS before being fixed in pure methanol for 20 min at −20° C. After three new rinses with PBS, treatment with bovine serum albumin (BSA) 5% in PBS (w/v) for 1 hour at room temperature to saturate the aspecific sites. The primary anti-α elastin antibody (polyclonal, rabbit, ab 21607, Abcam) diluted 1:200 in PBS/BSA at 0.5% (w/v) was incubated for 1 hour at room temperature. After three 5 min rinses in PBS, the secondary antibody anti-rabbit coupled to Alexa fluor 488 (Invitrogen® A11008) diluted ⅟600th in PBS/BSA 0.5% (w/v) was incubated for 1 h at room temperature and in the dark. Finally, the nuclei were countermarked with 4,6-Diamidino-2-phenylindole (DAPI) at 2 µg/ml in PBS for 10 min at room temperature. After five rinses with PBS, the slides were mounted in aqueous medium with a solution of Permafluor (LabVision, Thermoscientific). Images were acquired using the Nikon TE300 or Nikon TiE fluorescence microscopes.

Demonstration of the Role of Lysyl Oxidase in Complexation

The elastic polypeptide according to the invention (wild-type polypeptide) coupled to a fluorescent compound (rhodamine) was added to the post-confluent human dermal fibroblast culture medium (5 days) at a concentration of 1 µg/ml to evaluate its potential integration in the elastic fiber deposits (FIG. 11A). After 3 days, the cultures were stopped, the cells fixed and observation by fluorescence microscopy was performed. Under these conditions, the polypeptide is colocalized with fibrous deposits of tropoelastin (white arrow, FIG. 11B). This is not observed when the lysyl oxidase enzymes are previously inhibited by β-aminopropionitrile (350 µM) (FIG. 11C), demonstrating that the activity of the lysyl oxidase is necessary for the polypeptide to be complexed with the preexisting elastic fibers. These results demonstrate that the polypeptide is recognized as a substrate by lysyl oxidases. This result has never been demonstrated for any other elastic polypeptide.

Complexation of Mutated Polypeptides in the C-Terminus Domain

The hypothesis is that the unique ability of the polypeptide according to the invention to be integrated with the pre-existing elastic fibers is made possible by the presence of the D domain (GGACLGKACGRKRK, SEQ ID NO:6) at the C-terminus position, corresponding to the domain 36 of the human tropoelastin. For human tropoelastin, it has been shown that two particular motifs of this domain favor the incorporation and assembly within the elastic fibers: the RKRK motif (SEQ ID No: 5) and the formation of a disulfide bridge between the two cysteines separated by four amino acids (Nonaka R. et al, 2014).

In order to verify the functionality of these motifs in the polypeptide according to the invention, two mutants of the wild-type polypeptide were made. The first mutant, whose sequence is the sequence SEQ ID No: 13, relates to the last two amino acids of the polypeptide, resulting in the RKPR sequence (SEQ ID No: 22). The second mutant, whose sequence is the sequence SEQ ID No: 14, targets the first cysteine of the D domain, resulting in a glycine and preventing the formation of the disulfide bridge. The two mutant polypeptides were produced according to the protocol described in Example 1. The wild-type polypeptide and the two mutants coupled to rhodamine were added to the human dermal fibroblast culture medium (FIG. 12A), according to the protocol described previously in Example 6.

Figures 12A, 12B, 12C:
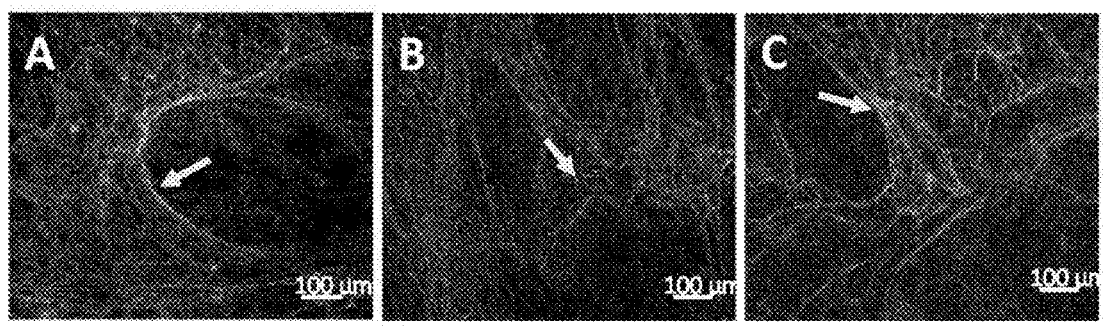
Figure 13:
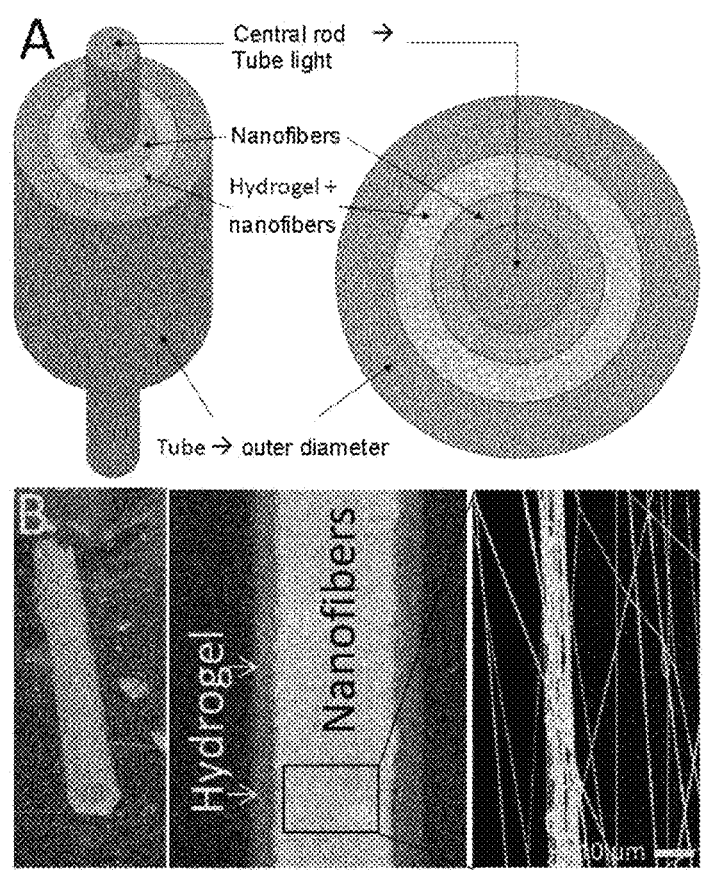

The wild-type polypeptide is integrated into large areas of preexisting or forming elastic fibers (FIG. 12A). This integration is very disturbed when the RKRK (SEQ ID No: 5) pattern is mutated to RKPR (SEQ ID No: 22) (FIG. 12B). This mutated version of the polypeptide only makes it possible to obtain small scattered aggregates along some elastic fibers (white arrow). On the other hand, the mutation of a cysteine preventing the formation of the disulfide bridge does not seem to affect the integration of the polypeptide into the elastic fibers (white arrow, FIG. 12C).

These results demonstrate the necessity of the presence of the domain D in the polypeptide according to the invention so that it is recognized and integrated into a network of elastic fibers formed by human dermal fibroblasts. More particularly, the pattern "RKRK" (SEQ ID No: 5) must be integral for this assembly to be effective. The disulfide bridge does not appear to be required in this particular method.

EXAMPLE 7: CREATION OF HYDROGEL/NANOFIBER COMPOSITES FOR VASCULAR SUBSTITUTES

Materials and Methods

The ease of shaping the hydrogels makes it easy to associate them with other materials, especially for the formation of composite hydrogel/nanofiber tubes intended to create vascular substitutes.

Nanofibers are produced by the jet-spraying technique (Sohier et al, 2014). Briefly, this method consists of diffracting polymer solutions by a stream of air to form nanofibers. A solution of polycaprolactone (PCL, molecular weight 80,000 g/mol) in chloroform is placed in a tank connected to a spraying apparatus by a tube. The spraying apparatus consists of a cone containing an adjustable position needle to control the opening of the cone. The tip of the cone is positioned in front of a tube distributing a flow of compressed air at different pressures. By creating a vacuum, the airflow drives the polymer solution from the reservoir to the tip of the cone through the needle, where it is diffracted and projected onto a target that collects solid fibers due to the evaporation of chloroform during the transit.

In order to form nanofiber tubular structures of different diameters and thicknesses, wherein the polymer is sprayed onto a glass tube previously dipped in a solution of dichloromethyl silane, of defined and variable diameter, in rotation at a defined speed of between 100 and 1000 rpm. The thickness is controlled by the spraying time. After creating a layer of nanofibers, the coated glass tubes are placed in a solution of 70% ethanol and then rinsed with phosphate buffered saline (PBS, 137 mM NaCl, 2.7 mM KCl, 10 mM $Na_2HPO_4$, 2 mM $KH_2PO_4$ pH 7.4) to render the polymer hydrophilic.

The hydrogel is prepared as defined in Example 3, with the following composition: DGL 50 mg/ml, PEG-NHS 50 mg/ml, PDE 3.75 mg/ml.

In order to form the composites, the glass tubes on which the nanofibers are deposited are placed horizontally inside a glass tube of defined and variable diameter, previously soaked in a solution of dichloromethyl silane. The inner glass tube is centered and the hydrogel composition is injected with a pipette between the walls of the two glass tubes. The hydrogel fills the available space and penetrates the nanofibrillary structure before crosslinking and thereby forming a composite of internal diameter controlled by the glass tube having collected the fibers; and with an external diameter controlled by the second glass tube (FIGS. 13A and 13B).

The composite tubes are removed by incubating the glass tubes in pure ethanol to remove the inner glass tube, which is then placed in pure water to remove the tubular hydrogel/nanofiber composite.

Results

Different hydrogel/nanofiber tubular composites could be created by creating polymer nanofiber tubes, followed by embedding and penetration of the hydrogel within the nanofibrillary matrix before crosslinking. The application of the hydrogel between two glass tubes made it possible to form composite tubes of internal lumen 1 and 2 mm and external diameter of 2 and 3 mm (FIG. 14).

The nanofibrillary tubes appear encased in the hydrogel (FIG. 14). Their diameter may be varied during their initial production by jet-spraying and these tubes may be integrated into hydrogel tubes of lower internal light, resulting in a positioning of the nanofiber layer between two hydrogel layers. Measurements made after the diameters of the composite tubes are in line with those expected from the diameters of the glass tubes used for manufacturing (FIG. 15).

Macroscopically, the tubes obtained do not delaminate and show greater resistance to elongation and rupture than similar tubes composed solely of the hydrogel.

BIBLIOGRAPHIC REFERENCES

Annabi N. et al (2013) *Elastomeric recombinant protein-based biomaterials*. Biochem. Eng. J. 77: p. 110-118.

Denkewalter R. G., et al (1981) *Macromolecular highly branched homogeneous compound based on lysine units*, in USP. 1981, Allied Corp.: US.

Denkewalter R. G. et al (1983) *Macromolecular highly branched homogeneous compound*, USP. 1983, Allied Corp. : US.

Jeon W. B. et al (2011) *Stimulation of fibroblasts and neuroblasts on a biomimetic extracellular matrix consisting of tandem repeats of the elastic VGVPG domain and RGD motif.* J. Biomed. Mater. Res. A. 97(2): p. 152-157.

Klok H. A. et al (2002) *Dendritic graft polypeptides.* Macromolecules, 35, p. 8718-8723.

Nonaka R. et al (2014) *Domain 36 of tropoelastin in elastic fiber formation.* Biol Pharm Bull 37 (2014) 698-702).

Rodriguez-Hernandez J., et al (2003) Highly Branched Poly (L-lysine), *Biomacromolecules,* 4: p. 249-258.

Pailler-Mattei et al (2013) In vivo skin biophysical behaviour and surface topography as a function of ageing, J. Mech. Behav. Biomed. Mater., December, 28, 474-83.

Rossi J. C. et al (2012) Functionalisation of free amino groups of lysine dendrigraft (DGL) polymers, *Tetrahedron Letters,* 53, p: 2976-2979.

Sohier J. et al (2014) *novel and simple alternative to create nanofibrillar matrices of interest for tissue engineering.* Tissue Engineering Part C-Methods, 2014. 20(4): p. 285-29

Wise S. G. et al (2014) Tropoelastin: a versatile, bioactive assembly module. *Acta Biomater,* 10, (4), 1532-41.

Yeo G. C. et al (2011) *Coacervation of tropoelastin.* Adv Colloid Interface Sci. 167(1-2): p. 94-103.

Yeo G. C. et al (2015) *Fabricated Elastin.* Advanced healthcare materials, 4(16): p. 2530-2556.

The invention claimed is:

1. An isolated polypeptide derived from tropoelastin comprising an amino acid sequence, wherein the amino acid sequence comprises, successively, from the N-terminus to the C-terminus of the polypeptide:
   a domain comprising at least 2 and at most 40 repeats of a unit comprising:
      a hydrophobic region (A) comprising successively at least 6 and at most 80 sequences of $X_1GX_2X_3PG$ (SEQ ID NO: 1)

wherein $X_1$, $X_2$ and $X_3$ represent a hydrophobic amino acid independently selected from the group consisting of: alanine, valine, leucine and isoleucine; wherein the SEQ ID No:1 is identical or different
   a region (B) comprising at least one of

AAAKAAK (SEQ ID NO: 2)

or

AAAKAAAKAAK; (SEQ ID NO: 3)

and
   a domain (D) comprising at least two non-consecutive cysteine amino acids and the sequence

RKRK, (SEQ ID NO: 5)

or the sequence

GGACLGKACGRKRK, (SEQ ID NO: 6)

or
   wherein the amino acid sequence comprises successively, from the N-terminus to the C-terminus of the polypeptide:
   a domain comprising at least 2 and at most 40 repeats of a unit comprising:
      a hydrophobic region (A) comprising successively at least 6 and at most 80 sequences of $X_1GX_2X_3PG$ (SEQ ID NO: 1)

wherein $X_1$, $X_2$ and $X_3$ represent a hydrophobic amino acid independently selected from the group consisting of: alanine, valine, leucine and isoleucine; wherein the SEQ ID No:1 is identical or different,
   a region (B) comprising at least one of

AAAKAAK (SEQ ID NO: 2)

or

AAAKAAAKAAK (SEQ ID NO: 3)

a hydrophobic domain (C) comprising successively at least 6 and at most 80 sequences of $X_4GX_5X_6PG$ (SEQ ID NO: 4)

wherein $X_4$, $X_5$ and $X_6$ are any hydrophobic amino acid except proline; and
   wherein the SEQ ID No:4 is identical or different; and
   a domain (D) comprising at least two non-consecutive cysteine amino acids and the sequence

RKRK, (SEQ ID NO: 5)

or

GGACLGKACGRKRK. (SEQ ID NO: 6)

2. The polypeptide according to claim 1, comprising the amino acid sequence of SEQ ID NO: 8.

3. A biocompatible material comprising the polypeptide according to claim 1.

4. The biocompatible material according to claim 3 further comprising a hydrophilic polymer.

5. The biocompatible material according to claim 4, wherein
   the polypeptide comprises the amino acid sequence of SEQ ID NO: 8,
   the polymer is a grafted dendrimer of polylysine of generation 3, and
   the biocompatible material comprises a bifunctional crosslinking agent comprising a polyethylene glycol (PEG) chain.

6. A composite biomaterial comprising the biocompatible material according to claim 4, and a compound selected from the group consisting of a synthetic material, a material of natural origin, and a mixture of a synthetic material and a material of natural origin.

7. The method for preparing the biocompatible material according to claim 3, comprising mixing the polypeptide according to claim 1 and a crosslinking agent.

8. The method for preparing the biocompatible material according to claim 7, wherein the crosslinking agent is a bifunctional agent and wherein the step of mixing the polypeptide and the crosslinking agent is carried out in the presence of a hydrophilic polymer.

9. The method for preparing the biocompatible material according to claim 7 further comprising:
   casting the biocompatible material in a mold of defined shape; and
   generating pores within the material, wherein the two steps may be successive, in any order, or simultaneous.

10. The method for preparing the biocompatible material according to claim 7 further comprising:
    contacting the mixture of the polypeptide according to claim 1 and a crosslinking agent with a compound consisting of a synthetic material, of a material of natural origin, or a mixture of synthetic materials and materials of natural origin.

11. A method for the preparation of a composite biomaterial comprising combining the biocompatible material according to claim 3 and a compound selected from the group consisting of a synthetic material, a material of natural origin, and a mixture of a synthetic material and a material of natural origin.

12. An in vitro cell culture support comprising the biocompatible material obtained by the method according to claim 9.

* * * * *

SEQUENCE LISTING

```
<160> NUMBER OF SEQ ID NOS: 18

<210> SEQ ID NO 1
<211> LENGTH: 6
<212> TYPE: PRT
<213> ORGANISM: Artificial Sequence
<220> FEATURE:
<223> OTHER INFORMATION: Hydrophobic consensus sequence
<220> FEATURE:
<221> NAME/KEY: MISC_FEATURE
<222> LOCATION: (1)..(1)
<223> OTHER INFORMATION: X est Ala, Val, Leu ou Ile.
<220> FEATURE:
<221> NAME/KEY: MISC_FEATURE
<222> LOCATION: (3)..(3)
<223> OTHER INFORMATION: X est Ala, Val, Leu ou Ile
<220> FEATURE:
<221> NAME/KEY: MISC_FEATURE
<222> LOCATION: (4)..(4)
<223> OTHER INFORMATION: X est Ala, Val, Leu ou Ile.

<400> SEQUENCE: 1

Xaa Gly Xaa Xaa Pro Gly
1               5

<210> SEQ ID NO 2
<211> LENGTH: 7
<212> TYPE: PRT
<213> ORGANISM: Artificial Sequence
<220> FEATURE:
<223> OTHER INFORMATION: Minimal sequence of crosslinking

<400> SEQUENCE: 2

Ala Ala Ala Lys Ala Ala Lys
1               5

<210> SEQ ID NO 3
<211> LENGTH: 11
<212> TYPE: PRT
<213> ORGANISM: Artificial Sequence
<220> FEATURE:
<223> OTHER INFORMATION: Crosslinking sequence

<400> SEQUENCE: 3

Ala Ala Ala Lys Ala Ala Ala Lys Ala Ala Lys
1               5                   10

<210> SEQ ID NO 4
<211> LENGTH: 6
<212> TYPE: PRT
<213> ORGANISM: Artificial Sequence
<220> FEATURE:
<223> OTHER INFORMATION: C-domain consensus sequence
<220> FEATURE:
<221> NAME/KEY: MISC_FEATURE
```

```
<222> LOCATION: (1)..(1)
<223> OTHER INFORMATION: X est Ala, Arg, Asn, Asp, Gln, Glu, Gly, His,
      Ile, Leu, Lys, Met, Phe, Trp, Ser, Thr, Tyr ou Val.
<220> FEATURE:
<221> NAME/KEY: MISC_FEATURE
<222> LOCATION: (3)..(3)
<223> OTHER INFORMATION: X est Ala, Arg, Asn, Asp, Gln, Glu, Gly, His,
      Ile, Leu, Lys, Met, Phe, Trp, Ser, Thr, Tyr ou Val.
<220> FEATURE:
<221> NAME/KEY: MISC_FEATURE
<222> LOCATION: (4)..(4)
<223> OTHER INFORMATION: X est Ala, Arg, Asn, Asp, Gln, Glu, Gly, His,
      Ile, Leu, Lys, Met, Phe, Trp, Ser, Thr, Tyr ou Val.

<400> SEQUENCE: 4

Xaa Gly Xaa Xaa Pro Gly
1               5

<210> SEQ ID NO 5
<211> LENGTH: 4
<212> TYPE: PRT
<213> ORGANISM: Artificial Sequence
<220> FEATURE:
<223> OTHER INFORMATION: Minimal C-terminal sequence

<400> SEQUENCE: 5

Arg Lys Arg Lys
1

<210> SEQ ID NO 6
<211> LENGTH: 14
<212> TYPE: PRT
<213> ORGANISM: Artificial Sequence
<220> FEATURE:
<223> OTHER INFORMATION: C-terminal sequence

<400> SEQUENCE: 6

Gly Gly Ala Cys Leu Gly Lys Ala Cys Gly Arg Lys Arg Lys
1               5                   10

<210> SEQ ID NO 7
<211> LENGTH: 6
<212> TYPE: PRT
<213> ORGANISM: Artificial Sequence
<220> FEATURE:
<223> OTHER INFORMATION: Hydrophobic consensus sequence
<220> FEATURE:
<221> NAME/KEY: MISC_FEATURE
<222> LOCATION: (4)..(4)
<223> OTHER INFORMATION: X est Ala ou Leu.

<400> SEQUENCE: 7

Val Gly Val Xaa Pro Gly
1               5

<210> SEQ ID NO 8
<211> LENGTH: 728
<212> TYPE: PRT
<213> ORGANISM: Artificial Sequence
<220> FEATURE:
<223> OTHER INFORMATION: Polypeptide

<400> SEQUENCE: 8

Val Gly Val Ala Pro Gly Val Gly Val Leu Pro Gly Val Gly Val Ala
1               5                   10                  15

Pro Gly Val Gly Val Leu Pro Gly Val Gly Val Ala Pro Gly Val Gly
            20                  25                  30

Val Leu Pro Gly Val Gly Val Ala Pro Gly Val Gly Val Leu Pro Gly
```

-continued

```
                35                  40                  45
Val Gly Val Ala Pro Gly Val Gly Val Leu Pro Gly Val Gly Val Ala
 50                  55                  60

Pro Gly Val Gly Val Leu Pro Gly Ala Ala Ala Lys Ala Ala Ala Lys
 65                  70                  75                  80

Ala Ala Lys Val Gly Val Ala Pro Gly Val Gly Val Leu Pro Gly Val
                 85                  90                  95

Gly Val Ala Pro Gly Val Gly Val Leu Pro Gly Val Gly Val Ala Pro
                100                 105                 110

Gly Val Gly Val Leu Pro Gly Val Gly Val Ala Pro Gly Val Gly Val
            115                 120                 125

Leu Pro Gly Val Gly Val Ala Pro Gly Val Gly Val Leu Pro Gly Val
130                 135                 140

Gly Val Ala Pro Gly Val Gly Val Leu Pro Gly Ala Ala Ala Lys Ala
145                 150                 155                 160

Ala Ala Lys Ala Ala Lys Val Gly Val Ala Pro Gly Val Gly Val Leu
            165                 170                 175

Pro Gly Val Gly Val Ala Pro Gly Val Gly Val Leu Pro Gly Val Gly
            180                 185                 190

Val Ala Pro Gly Val Gly Val Leu Pro Gly Val Gly Val Ala Pro Gly
        195                 200                 205

Val Gly Val Leu Pro Gly Val Gly Val Ala Pro Gly Val Gly Val Leu
    210                 215                 220

Pro Gly Val Gly Val Ala Pro Gly Val Gly Val Leu Pro Gly Ala Ala
225                 230                 235                 240

Ala Lys Ala Ala Ala Lys Ala Ala Lys Val Gly Val Ala Pro Gly Val
                245                 250                 255

Gly Val Leu Pro Gly Val Gly Val Ala Pro Gly Val Gly Val Leu Pro
            260                 265                 270

Gly Val Gly Val Ala Pro Gly Val Gly Val Leu Pro Gly Val Gly Val
            275                 280                 285

Ala Pro Gly Val Gly Val Leu Pro Gly Val Gly Val Ala Pro Gly Val
        290                 295                 300

Gly Val Leu Pro Gly Val Gly Val Ala Pro Gly Val Gly Val Leu Pro
305                 310                 315                 320

Gly Ala Ala Ala Lys Ala Ala Lys Ala Ala Lys Val Gly Val Ala
                325                 330                 335

Pro Gly Val Gly Val Leu Pro Gly Val Gly Val Ala Pro Gly Val Gly
            340                 345                 350

Val Leu Pro Gly Val Gly Val Ala Pro Gly Val Gly Val Leu Pro Gly
        355                 360                 365

Val Gly Val Ala Pro Gly Val Gly Val Leu Pro Gly Val Gly Val Ala
    370                 375                 380

Pro Gly Val Gly Val Leu Pro Gly Val Gly Val Ala Pro Gly Val Gly
385                 390                 395                 400

Val Leu Pro Gly Ala Ala Ala Lys Ala Ala Lys Ala Ala Lys Val
                405                 410                 415

Gly Val Ala Pro Gly Val Gly Val Leu Pro Gly Val Gly Val Ala Pro
            420                 425                 430

Gly Val Gly Val Leu Pro Gly Val Gly Val Ala Pro Gly Val Gly Val
            435                 440                 445

Leu Pro Gly Val Gly Val Ala Pro Gly Val Gly Val Leu Pro Gly Val
450                 455                 460
```

Gly Val Ala Pro Gly Val Gly Val Leu Pro Gly Val Gly Val Ala Pro
465                 470                 475                 480

Gly Val Gly Val Leu Pro Gly Ala Ala Ala Lys Ala Ala Ala Lys Ala
                485                 490                 495

Ala Lys Val Gly Val Ala Pro Gly Val Gly Val Leu Pro Gly Val Gly
            500                 505                 510

Val Ala Pro Gly Val Gly Val Leu Pro Gly Val Gly Val Ala Pro Gly
        515                 520                 525

Val Gly Val Leu Pro Gly Val Gly Val Ala Pro Gly Val Gly Val Leu
    530                 535                 540

Pro Gly Val Gly Val Ala Pro Gly Val Gly Val Leu Pro Gly Val Gly
545                 550                 555                 560

Val Ala Pro Gly Val Gly Val Leu Pro Gly Val Gly Val Ala Pro Gly
                565                 570                 575

Val Gly Val Leu Pro Gly Val Gly Val Ala Pro Gly Val Gly Val Leu
            580                 585                 590

Pro Gly Val Gly Val Ala Pro Gly Val Gly Val Leu Pro Gly Val Gly
        595                 600                 605

Val Ala Pro Gly Val Gly Val Leu Pro Gly Val Gly Val Ala Pro Gly
    610                 615                 620

Val Gly Val Leu Pro Gly Val Gly Val Ala Pro Gly Val Gly Val Leu
625                 630                 635                 640

Pro Gly Val Gly Val Ala Pro Gly Val Gly Val Leu Pro Gly Val Gly
                645                 650                 655

Val Ala Pro Gly Val Gly Val Leu Pro Gly Val Gly Val Ala Pro Gly
            660                 665                 670

Val Gly Val Leu Pro Gly Val Gly Val Ala Pro Gly Val Gly Val Leu
        675                 680                 685

Pro Gly Val Gly Val Ala Pro Gly Val Gly Val Leu Pro Gly Val Gly
    690                 695                 700

Val Ala Pro Gly Val Gly Val Leu Pro Gly Gly Gly Ala Cys Leu Gly
705                 710                 715                 720

Lys Ala Cys Gly Arg Lys Arg Lys
                725

<210> SEQ ID NO 9
<211> LENGTH: 737
<212> TYPE: PRT
<213> ORGANISM: Artificial Sequence
<220> FEATURE:
<223> OTHER INFORMATION: Polypeptide preceded by Flag

<400> SEQUENCE: 9

Cys Asp Tyr Lys Asp Asp Asp Lys Val Gly Val Ala Pro Gly Val
1               5                   10                  15

Gly Val Leu Pro Gly Val Gly Val Ala Pro Gly Val Gly Val Leu Pro
                20                  25                  30

Gly Val Gly Val Ala Pro Gly Val Gly Val Leu Pro Gly Val Gly Val
            35                  40                  45

Ala Pro Gly Val Gly Val Leu Pro Gly Val Gly Val Ala Pro Gly Val
        50                  55                  60

Gly Val Leu Pro Gly Val Gly Val Ala Pro Gly Val Gly Val Leu Pro
65                  70                  75                  80

Gly Ala Ala Ala Lys Ala Ala Lys Ala Ala Lys Val Gly Val Ala
                85                  90                  95

```
Pro Gly Val Gly Val Leu Pro Gly Val Gly Val Ala Pro Gly Val Gly
            100                 105                 110

Val Leu Pro Gly Val Gly Val Ala Pro Gly Val Gly Val Leu Pro Gly
        115                 120                 125

Val Gly Val Ala Pro Gly Val Gly Val Leu Pro Gly Val Gly Val Ala
    130                 135                 140

Pro Gly Val Gly Val Leu Pro Gly Val Gly Val Ala Pro Gly Val Gly
145                 150                 155                 160

Val Leu Pro Gly Ala Ala Ala Lys Ala Ala Lys Ala Ala Lys Val
        165                 170                 175

Gly Val Ala Pro Gly Val Gly Val Leu Pro Gly Val Gly Val Ala Pro
            180                 185                 190

Gly Val Gly Val Leu Pro Gly Val Gly Val Ala Pro Gly Val Gly Val
        195                 200                 205

Leu Pro Gly Val Gly Val Ala Pro Gly Val Gly Val Leu Pro Gly Val
    210                 215                 220

Gly Val Ala Pro Gly Val Gly Val Leu Pro Gly Val Gly Val Ala Pro
225                 230                 235                 240

Gly Val Gly Val Leu Pro Gly Ala Ala Ala Lys Ala Ala Lys Ala
        245                 250                 255

Ala Lys Val Gly Val Ala Pro Gly Val Gly Val Leu Pro Gly Val Gly
            260                 265                 270

Val Ala Pro Gly Val Gly Val Leu Pro Gly Val Gly Val Ala Pro Gly
        275                 280                 285

Val Gly Val Leu Pro Gly Val Gly Val Ala Pro Gly Val Gly Val Leu
    290                 295                 300

Pro Gly Val Gly Val Ala Pro Gly Val Gly Val Leu Pro Gly Val Gly
305                 310                 315                 320

Val Ala Pro Gly Val Gly Val Leu Pro Gly Ala Ala Ala Lys Ala Ala
        325                 330                 335

Ala Lys Ala Ala Lys Val Gly Val Ala Pro Gly Val Gly Val Leu Pro
            340                 345                 350

Gly Val Gly Val Ala Pro Gly Val Gly Val Leu Pro Gly Val Gly Val
        355                 360                 365

Ala Pro Gly Val Gly Val Leu Pro Gly Val Gly Val Ala Pro Gly Val
    370                 375                 380

Gly Val Leu Pro Gly Val Gly Val Ala Pro Gly Val Gly Val Leu Pro
385                 390                 395                 400

Gly Val Gly Val Ala Pro Gly Val Gly Val Leu Pro Gly Ala Ala Ala
        405                 410                 415

Lys Ala Ala Lys Ala Ala Lys Val Gly Val Ala Pro Gly Val Gly
            420                 425                 430

Val Leu Pro Gly Val Gly Val Ala Pro Gly Val Gly Val Leu Pro Gly
        435                 440                 445

Val Gly Val Ala Pro Gly Val Gly Val Leu Pro Gly Val Gly Val Ala
    450                 455                 460

Pro Gly Val Gly Val Leu Pro Gly Val Gly Val Ala Pro Gly Val Gly
465                 470                 475                 480

Val Leu Pro Gly Val Gly Val Ala Pro Gly Val Gly Val Leu Pro Gly
        485                 490                 495

Ala Ala Ala Lys Ala Ala Lys Ala Ala Lys Val Gly Val Ala Pro
            500                 505                 510
```

```
Gly Val Gly Val Leu Pro Gly Val Gly Val Ala Pro Gly Val Gly Val
            515                 520                 525
Leu Pro Gly Val Gly Val Ala Pro Gly Val Gly Val Leu Pro Gly Val
        530                 535                 540
Gly Val Ala Pro Gly Val Gly Val Leu Pro Gly Val Gly Val Ala Pro
545                 550                 555                 560
Gly Val Gly Val Leu Pro Gly Val Gly Val Ala Pro Gly Val Gly Val
            565                 570                 575
Leu Pro Gly Val Gly Val Ala Pro Gly Val Gly Val Leu Pro Gly Val
        580                 585                 590
Gly Val Ala Pro Gly Val Gly Val Leu Pro Gly Val Gly Val Ala Pro
            595                 600                 605
Gly Val Gly Val Leu Pro Gly Val Gly Val Ala Pro Gly Val Gly Val
            610                 615                 620
Leu Pro Gly Val Gly Val Ala Pro Gly Val Gly Val Leu Pro Gly Val
625                 630                 635                 640
Gly Val Ala Pro Gly Val Gly Val Leu Pro Gly Val Gly Val Ala Pro
            645                 650                 655
Gly Val Gly Val Leu Pro Gly Val Gly Val Ala Pro Gly Val Gly Val
            660                 665                 670
Leu Pro Gly Val Gly Val Ala Pro Gly Val Gly Val Leu Pro Gly Val
        675                 680                 685
Gly Val Ala Pro Gly Val Gly Val Leu Pro Gly Val Gly Val Ala Pro
        690                 695                 700
Gly Val Gly Val Leu Pro Gly Val Gly Val Ala Pro Gly Val Gly Val
705                 710                 715                 720
Leu Pro Gly Gly Gly Ala Cys Leu Gly Lys Ala Cys Gly Arg Lys Arg
                725                 730                 735
Lys

<210> SEQ ID NO 10
<211> LENGTH: 12
<212> TYPE: PRT
<213> ORGANISM: Artificial Sequence
<220> FEATURE:
<223> OTHER INFORMATION: Dodecapeptide motif

<400> SEQUENCE: 10

Val Gly Val Ala Pro Gly Val Gly Val Leu Pro Gly
1               5                   10

<210> SEQ ID NO 11
<211> LENGTH: 1767
<212> TYPE: DNA
<213> ORGANISM: Artificial Sequence
<220> FEATURE:
<223> OTHER INFORMATION: Sequence coding for polypeptide

<400> SEQUENCE: 11
catatgtgtg actacaaaga tgatgatgat aaagttggcg ttgctccggg cgttggcgtg      60
ctgccgggcg ttggcgttgc tccgggcgtt ggcgtgctgc cgggtgtggg tgttgcaccg     120
ggtgtcggtg tgctgccggg tgttggcgtc gctccgggtg tgggtgttct gccgggtgtc     180
ggtgtggcac cgggtgttgg cgtcctgccg gtgtgggcg tggccccggg cgttggtgtg     240
ctgccgggtc agccgcaaa agctgcggcc aaagcagcta aggttggtgt cgcaccgggc     300
gttggcgttc tgccgggcgt cggtgtggct ccgggtgttg gtgtcctgcc gggcgttggt     360
```

```
gtggccccgg gtgtcggcgt gctgccgggt gttggtgtcg caccgggtgt tggcgtgctg    420
ccgggtgtcg gcgttgcacc gggcgtgggt gtcctgccgg cgtcggtgt tgctccgggc     480 gtgggcgttc tgccgggtgc agcagcaaag ccgccgcga aggccgccaa agtgggtgtc     540
gcaccgggcg tcggcgtcct gccgggtgtc ggcgtggccc cgggtgtggg cgtgctgccg    600
ggcgtgggcg tggccccggg tgttggtgtt ctgccgggcg tgggtgttgc ccgggcgtt    660 ggtgtcctgc cgggtgttgg cgttgccccg gtgtgggtg tgctgccggg tgtgggcgtc    720
gccccgggcg tgggcgtcct gccgggcgcc gcggccaagg ccgccgcgaa ggcggccaaa    780
gtcggcgtcg caccgggcgt tggtgttctg ccgggtgttg gcgtggcgcc gggcgtcggc    840
gttctgccgg gtgttggtgt ggcgccgggc gtgggcgtat accgggtgt gggcgtcgca    900 ccgggcgtcg gtgtcctgcc gggcgtgggt gtcgccccgg gtgtgggcgt cctgccgggt    960
gttggtgttg ccccgggcgt gggcgtgctg ccggtgccg ccgccaaggc cgccgcgaaa   1020
gccgccaaag tcggtgttgc accgggtgtt ggcgttctgc cgggtgtggg tgtcgcgcct   1080
ggcgttggag ttttacctgg cgtgggtgtc cgcccgggcg tgggtggtgt tggagttta    1140 cctggtgttg gtgtcgcccc gggtgtcggc gttttacctg gtgtcggtgt cgccccgggc   1200
gtgggtgtgc tgccgggcgc agcagccaag ccgccgcta aggccgccaa agtcggtgtc   1260
gcacctggtg ttggtgtgct gccgggcgtc ggcgttgcgc ctggtgttgg agttcttcct   1320
ggtgtgggcg ttgcaccggg agtgggcgtg ttacctggtg ttggcgtcgc ccctggcgtc   1380
ggagtgttac cgggcgttgg tgtggcgccg ggtgtcggcg tattaccggg cgttggcgtc   1440
gcccctggag tcggcgtgct gccgggcgcc gcggcgaagg ccgccgccaa agcagctaaa   1500
gttggcgtcg ccctgggt cggtgtgtta ccggcgtcg gcgtggcgcc gggtgtcgga    1560
gtcttaccgg gcgtgggcgt ggcgcctggc gtcggtgttc tgccgggtgt gggcgttgcg   1620
ccgggcgtag gcgttttacc cggtgtgggt gtcgcgccgg gtgtgggtgt cctgccgggt   1680
gtcggtgttg cccctggcgt cggtgtatta ccgggcggtg gcgcgtgcct gggtaaagcc   1740
tgtggccgta aacgcaagta agtcgac                                       1767
```

<210> SEQ ID NO 12
<211> LENGTH: 1794
<212> TYPE: DNA
<213> ORGANISM: Artificial Sequence
<220> FEATURE:
<223> OTHER INFORMATION: Sequence coding for polypeptide (with C and Flag)

<400> SEQUENCE: 12

```
catatgtgtg actacaaaga tgatgatgat aaagttggcg ttgctccggg cgttggcgtg     60
ctgccgggcg ttggcgttgc tccgggcgtt ggcgtgctgc cgggtgtggg tgttgcaccg    120
ggtgtcggtg tgctgccggg tgttggcgtc gctccgggtg tgggtgttct gccgggtgtc    180
ggtgtggcac cgggtgttgg cgtcctgccg ggtgtgggc tggccccggg cgttggtgtg    240
ctgccgggtg cagccgcaaa agctgcggcc aaagcagcta aggttggtgt cgcaccgggc    300
gttggcgttc tgccgggcgt cggtgtggct ccgggtgttg gtgtcctgcc gggcgttggt    360
gtggccccgg gtgtcggcgt gctgccgggt gttggtgtcg caccgggtgt tggcgtgctg    420
ccgggtgtcg gcgttgcacc gggcgtgggt gtcctgccgg cgtcggtgt tgctccgggc     480 gtgggcgttc tgccgggtgc agcagcaaag ccgccgcga aggccgccaa agtgggtgtc     540
gcaccgggcg tcggcgtcct gccgggtgtc ggcgtggccc cgggtgtggg cgtgctgccg    600
```

| | |
|---|---|
| ggcgtgggcg tggccccggg tgttggtgtt ctgccgggcg tgggtgttgc cccgggcgtt | 660 |
| ggtgtcctgc cgggtgttgg cgttgccccg ggtgtgggtg tgctgccggg tgtgggcgtc | 720 |
| gccccgggcg tgggcgtcct gccgggcgcc gcggccaagg ccgccgcgaa ggcggccaaa | 780 |
| gtcggcgtcg caccgggcgt tggtgttctg ccgggtgttg gcgtggcgcc gggcgtcggc | 840 |
| gttctgccgg gtgttggtgt ggcgccgggc gtgggcgtat accgggtgt gggcgtcgca | 900 |
| ccgggcgtcg gtgtcctgcc gggcgtgggt gtcgccccgg gtgtgggcgt cctgccgggt | 960 |
| gttggtgttg ccccgggcgt gggcgtgctg ccgggtgccg ccgccaaggc cgccgcgaaa | 1020 |
| gccgccaaag tcggtgttgc accgggtgtt ggcgttctgc cgggtgtggg tgtcgcgcct | 1080 |
| ggcgttggag ttttacctgg cgtgggtgtc cgccgggcg tgggtgttct gccgggcgtt | 1140 |
| ggcgtggcac ctggtgttgg agttttacct ggtgttggtg tcgccccggg tgtcggcgtt | 1200 |
| ttacctggtg tcggtgtcgc cccgggcgtg gtgtgctgc cgggcgcagc agccaaggcc | 1260 |
| gccgctaagg ccgccaaagt cggtgtcgca cctggtgttg gtgtgctgcc gggcgtcggc | 1320 |
| gttgcgcctg gtgttggagt tcttcctggt gtgggcgttg caccgggagt gggcgtgtta | 1380 |
| cctggtgttg gcgtcgcccc tggcgtcgga gtgttaccgg gcgttggtgt ggcgccgggt | 1440 |
| gtcggcgtat accgggcgt tggcgtcgcc cctggagtcg gcgtgctgcc gggcgccgcg | 1500 |
| gcgaaggccg ccgccaaagc agctaaagtt ggcgtcgccc ctggggtcgg tgtgttaccg | 1560 |
| ggcgtcggcg tggcgccggg tgtcggagtc ttaccgggcg tgggcgtggc gcctggcgtc | 1620 |
| ggtgttctgc cgggtgtggg cgttgcgccg ggcgtaggcg ttttaccccgg tgtgggtgtc | 1680 |
| gcgccgggtg tgggtgtcct gccgggtgtc ggtgttgccc ctggcgtcgg tgtattaccg | 1740 |
| ggcggtggcg cgtgcctggg taaagcctgt ggccgtaaac gcaagtaagt cgac | 1794 |

<210> SEQ ID NO 13
<211> LENGTH: 728
<212> TYPE: PRT
<213> ORGANISM: Artificial Sequence
<220> FEATURE:
<223> OTHER INFORMATION: Mutated polypeptide No1

<400> SEQUENCE: 13

Val Gly Val Ala Pro Gly Val Gly Val Leu Pro Gly Val Gly Val Ala
1               5                   10                  15

Pro Gly Val Gly Val Leu Pro Gly Val Gly Val Ala Pro Gly Val Gly
            20                  25                  30

Val Leu Pro Gly Val Gly Val Ala Pro Gly Val Gly Val Leu Pro Gly
        35                  40                  45

Val Gly Val Ala Pro Gly Val Gly Val Leu Pro Gly Val Gly Val Ala
    50                  55                  60

Pro Gly Val Gly Val Leu Pro Gly Ala Ala Ala Lys Ala Ala Ala Lys
65                  70                  75                  80

Ala Ala Lys Val Gly Val Ala Pro Gly Val Gly Val Leu Pro Gly Val
                85                  90                  95

Gly Val Ala Pro Gly Val Gly Val Leu Pro Gly Val Gly Val Ala Pro
            100                 105                 110

Gly Val Gly Val Leu Pro Gly Val Gly Val Ala Pro Gly Val Gly Val
        115                 120                 125

Leu Pro Gly Val Gly Val Ala Pro Gly Val Gly Val Leu Pro Gly Val
    130                 135                 140

Gly Val Ala Pro Gly Val Gly Val Leu Pro Gly Ala Ala Ala Lys Ala
145                 150                 155                 160

```
Ala Ala Lys Ala Ala Lys Val Gly Val Ala Pro Gly Val Gly Val Leu
            165                 170                 175

Pro Gly Val Gly Val Ala Pro Gly Val Gly Val Leu Pro Gly Val Gly
            180                 185                 190

Val Ala Pro Gly Val Gly Val Leu Pro Gly Val Gly Val Ala Pro Gly
        195                 200                 205

Val Gly Val Leu Pro Gly Val Gly Val Ala Pro Gly Val Gly Val Leu
        210                 215                 220

Pro Gly Val Gly Val Ala Pro Gly Val Gly Val Leu Pro Gly Ala Ala
225                 230                 235                 240

Ala Lys Ala Ala Lys Ala Ala Lys Val Gly Val Ala Pro Gly Val
            245                 250                 255

Gly Val Leu Pro Gly Val Gly Val Ala Pro Gly Val Gly Val Leu Pro
            260                 265                 270

Gly Val Gly Val Ala Pro Gly Val Gly Val Leu Pro Gly Val Gly Val
        275                 280                 285

Ala Pro Gly Val Gly Val Leu Pro Gly Val Gly Val Ala Pro Gly Val
        290                 295                 300

Gly Val Leu Pro Gly Val Gly Val Ala Pro Gly Val Gly Val Leu Pro
305                 310                 315                 320

Gly Ala Ala Ala Lys Ala Ala Lys Ala Ala Lys Val Gly Val Ala
            325                 330                 335

Pro Gly Val Gly Val Leu Pro Gly Val Gly Val Ala Pro Gly Val Gly
            340                 345                 350

Val Leu Pro Gly Val Gly Val Ala Pro Gly Val Gly Val Leu Pro Gly
        355                 360                 365

Val Gly Val Ala Pro Gly Val Gly Val Leu Pro Gly Val Gly Val Ala
        370                 375                 380

Pro Gly Val Gly Val Leu Pro Gly Val Gly Val Ala Pro Gly Val Gly
385                 390                 395                 400

Val Leu Pro Gly Ala Ala Ala Lys Ala Ala Lys Ala Ala Lys Val
            405                 410                 415

Gly Val Ala Pro Gly Val Gly Val Leu Pro Gly Val Gly Val Ala Pro
            420                 425                 430

Gly Val Gly Val Leu Pro Gly Val Gly Val Ala Pro Gly Val Gly Val
        435                 440                 445

Leu Pro Gly Val Gly Val Ala Pro Gly Val Gly Val Leu Pro Gly Val
        450                 455                 460

Gly Val Ala Pro Gly Val Gly Val Leu Pro Gly Val Gly Val Ala Pro
465                 470                 475                 480

Gly Val Gly Val Leu Pro Gly Ala Ala Ala Lys Ala Ala Ala Lys Ala
            485                 490                 495

Ala Lys Val Gly Val Ala Pro Gly Val Gly Val Leu Pro Gly Val Gly
            500                 505                 510

Val Ala Pro Gly Val Gly Val Leu Pro Gly Val Gly Val Ala Pro Gly
        515                 520                 525

Val Gly Val Leu Pro Gly Val Gly Val Ala Pro Gly Val Gly Val Leu
        530                 535                 540

Pro Gly Val Gly Val Ala Pro Gly Val Gly Val Leu Pro Gly Val Gly
545                 550                 555                 560

Val Ala Pro Gly Val Gly Val Leu Pro Gly Val Gly Val Ala Pro Gly
            565                 570                 575
```

-continued

```
Val Gly Val Leu Pro Gly Val Gly Val Ala Pro Gly Val Gly Val Leu
            580                 585                 590

Pro Gly Val Gly Val Ala Pro Gly Val Gly Val Leu Pro Gly Val Gly
        595                 600                 605

Val Ala Pro Gly Val Gly Val Leu Pro Gly Val Gly Val Ala Pro Gly
    610                 615                 620

Val Gly Val Leu Pro Gly Val Gly Val Ala Pro Gly Val Gly Val Leu
625                 630                 635                 640

Pro Gly Val Gly Val Ala Pro Gly Val Gly Val Leu Pro Gly Val Gly
            645                 650                 655

Val Ala Pro Gly Val Gly Val Leu Pro Gly Val Gly Val Ala Pro Gly
        660                 665                 670

Val Gly Val Leu Pro Gly Val Gly Val Ala Pro Gly Val Gly Val Leu
    675                 680                 685

Pro Gly Val Gly Val Ala Pro Gly Val Gly Val Leu Pro Gly Val Gly
690                 695                 700

Val Ala Pro Gly Val Gly Val Leu Pro Gly Gly Gly Ala Cys Leu Gly
            705                 710                 715                 720

Lys Ala Cys Gly Arg Lys Pro Arg
                725

<210> SEQ ID NO 14
<211> LENGTH: 728
<212> TYPE: PRT
<213> ORGANISM: Artificial Sequence
<220> FEATURE:
<223> OTHER INFORMATION: Mutated polypeptide No2

<400> SEQUENCE: 14

Val Gly Val Ala Pro Gly Val Gly Val Leu Pro Gly Val Gly Val Ala
1               5                   10                  15

Pro Gly Val Gly Val Leu Pro Gly Val Gly Val Ala Pro Gly Val Gly
            20                  25                  30

Val Leu Pro Gly Val Gly Val Ala Pro Gly Val Gly Val Leu Pro Gly
        35                  40                  45

Val Gly Val Ala Pro Gly Val Gly Val Leu Pro Gly Val Gly Val Ala
    50                  55                  60

Pro Gly Val Gly Val Leu Pro Gly Ala Ala Lys Ala Ala Ala Lys
65                  70                  75                  80

Ala Ala Lys Val Gly Val Ala Pro Gly Val Gly Val Leu Pro Gly Val
                85                  90                  95

Gly Val Ala Pro Gly Val Gly Val Leu Pro Gly Val Gly Val Ala Pro
            100                 105                 110

Gly Val Gly Val Leu Pro Gly Val Gly Val Ala Pro Gly Val Gly Val
        115                 120                 125

Leu Pro Gly Val Gly Val Ala Pro Gly Val Gly Val Leu Pro Gly Val
    130                 135                 140

Gly Val Ala Pro Gly Val Gly Val Leu Pro Gly Ala Ala Lys Ala
145                 150                 155                 160

Ala Ala Lys Ala Ala Lys Val Gly Val Ala Pro Gly Val Gly Val Leu
                165                 170                 175

Pro Gly Val Gly Val Ala Pro Gly Val Gly Val Leu Pro Gly Val Gly
            180                 185                 190

Val Ala Pro Gly Val Gly Val Leu Pro Gly Val Gly Val Ala Pro Gly
        195                 200                 205
```

-continued

Val Gly Val Leu Pro Gly Val Gly Val Ala Pro Gly Val Gly Val Leu
    210                 215                 220

Pro Gly Val Gly Val Ala Pro Gly Val Gly Val Leu Pro Gly Ala Ala
225                 230                 235                 240

Ala Lys Ala Ala Lys Ala Ala Lys Val Gly Val Ala Pro Gly Val
            245                 250                 255

Gly Val Leu Pro Gly Val Gly Val Ala Pro Gly Val Gly Val Leu Pro
            260                 265                 270

Gly Val Gly Val Ala Pro Gly Val Gly Val Leu Pro Gly Val Gly Val
            275                 280                 285

Ala Pro Gly Val Gly Val Leu Pro Gly Val Gly Val Ala Pro Gly Val
290                 295                 300

Gly Val Leu Pro Gly Val Gly Val Ala Pro Gly Val Gly Val Leu Pro
305                 310                 315                 320

Gly Ala Ala Ala Lys Ala Ala Lys Ala Ala Lys Val Gly Val Ala
            325                 330                 335

Pro Gly Val Gly Val Leu Pro Gly Val Gly Val Ala Pro Gly Val Gly
            340                 345                 350

Val Leu Pro Gly Val Gly Val Ala Pro Gly Val Gly Val Leu Pro Gly
            355                 360                 365

Val Gly Val Ala Pro Gly Val Gly Val Leu Pro Gly Val Gly Val Ala
            370                 375                 380

Pro Gly Val Gly Val Leu Pro Gly Val Gly Val Ala Pro Gly Val Gly
385                 390                 395                 400

Val Leu Pro Gly Ala Ala Ala Lys Ala Ala Lys Ala Ala Lys Val
            405                 410                 415

Gly Val Ala Pro Gly Val Gly Val Leu Pro Gly Val Gly Val Ala Pro
            420                 425                 430

Gly Val Gly Val Leu Pro Gly Val Gly Val Ala Pro Gly Val Gly Val
            435                 440                 445

Leu Pro Gly Val Gly Val Ala Pro Gly Val Gly Val Leu Pro Gly Val
            450                 455                 460

Gly Val Ala Pro Gly Val Gly Val Leu Pro Gly Val Gly Val Ala Pro
465                 470                 475                 480

Gly Val Gly Val Leu Pro Gly Ala Ala Ala Lys Ala Ala Ala Lys Ala
            485                 490                 495

Ala Lys Val Gly Val Ala Pro Gly Val Gly Val Leu Pro Gly Val Gly
            500                 505                 510

Val Ala Pro Gly Val Gly Val Leu Pro Gly Val Gly Val Ala Pro Gly
            515                 520                 525

Val Gly Val Leu Pro Gly Val Gly Val Ala Pro Gly Val Gly Val Leu
            530                 535                 540

Pro Gly Val Gly Val Ala Pro Gly Val Gly Val Leu Pro Gly Val Gly
545                 550                 555                 560

Val Ala Pro Gly Val Gly Val Leu Pro Gly Val Gly Val Ala Pro Gly
            565                 570                 575

Val Gly Val Leu Pro Gly Val Gly Val Ala Pro Gly Val Gly Val Leu
            580                 585                 590

Pro Gly Val Gly Val Ala Pro Gly Val Gly Val Leu Pro Gly Val Gly
            595                 600                 605

Val Ala Pro Gly Val Gly Val Leu Pro Gly Val Gly Val Ala Pro Gly
            610                 615                 620

Val Gly Val Leu Pro Gly Val Gly Val Ala Pro Gly Val Gly Val Leu

```
                625                 630                 635                 640
Pro Gly Val Gly Val Ala Pro Gly Val Gly Val Leu Pro Gly Val Gly
                    645                 650                 655
Val Ala Pro Gly Val Gly Val Leu Pro Gly Val Gly Val Ala Pro Gly
                660                 665                 670
Val Gly Val Leu Pro Gly Val Gly Val Ala Pro Gly Val Gly Val Leu
            675                 680                 685
Pro Gly Val Gly Val Ala Pro Gly Val Gly Val Leu Pro Gly Val Gly
        690                 695                 700
Val Ala Pro Gly Val Gly Val Leu Pro Gly Gly Gly Ala Gly Leu Gly
705                 710                 715                 720
Lys Ala Cys Gly Arg Lys Arg Lys
            725

<210> SEQ ID NO 15
<211> LENGTH: 40
<212> TYPE: DNA
<213> ORGANISM: Artificial
<220> FEATURE:
<223> OTHER INFORMATION: Sense probe mutant No1

<400> SEQUENCE: 15
aagcctgtgg ccgtaaacct aggtaagtcg acaagcttgc                            40

<210> SEQ ID NO 16
<211> LENGTH: 40
<212> TYPE: DNA
<213> ORGANISM: Artificial
<220> FEATURE:
<223> OTHER INFORMATION: Antisense probe mutant No1

<400> SEQUENCE: 16
gcaagcttgt cgacttacct aggtttacgg ccacaggctt                            40

<210> SEQ ID NO 17
<211> LENGTH: 29
<212> TYPE: DNA
<213> ORGANISM: Artificial
<220> FEATURE:
<223> OTHER INFORMATION: Sense probe mutant No2

<400> SEQUENCE: 17
gcgtttacgg ccaccggctt tacccaggc                                       29

<210> SEQ ID NO 18
<211> LENGTH: 29
<212> TYPE: DNA
<213> ORGANISM: Artificial
<220> FEATURE:
<223> OTHER INFORMATION: Antisense probe mutant No2

<400> SEQUENCE: 18
gcctgggtaa agccggtggc cgtaaacgc                                       29
```